(12) United States Patent
Choi et al.

(10) Patent No.: US 10,918,717 B2
(45) Date of Patent: Feb. 16, 2021

(54) PHARMACEUTICAL FORMULATION COMPRISING ANTI-EGFR ANTIBODY

(71) Applicant: GREEN CROSS CORPORATION, Yongin-si (KR)

(72) Inventors: Yong Woon Choi, Yongin-si (KR); Yoo Hoon Kim, Yongin-si (KR); Jungsub Choi, Yongin-si (KR)

(73) Assignee: GREEN CROSS CORPORATION, Yongin (KR)

( * ) Notice: Subject to any disclaimer, the term of this patent is extended or adjusted under 35 U.S.C. 154(b) by 242 days.

(21) Appl. No.: 15/544,335

(22) PCT Filed: Jan. 15, 2016

(86) PCT No.: PCT/KR2016/000472
§ 371 (c)(1),
(2) Date: Jul. 18, 2017

(87) PCT Pub. No.: WO2016/117883
PCT Pub. Date: Jul. 28, 2016

(65) Prior Publication Data
US 2017/0368175 A1    Dec. 28, 2017

(30) Foreign Application Priority Data

Jan. 19, 2015   (KR) .......................... 10-2015-0008677

(51) Int. Cl.
*A61K 39/395* (2006.01)
*C07K 16/28* (2006.01)
(Continued)

(52) U.S. Cl.
CPC .... *A61K 39/39591* (2013.01); *A61K 39/3955* (2013.01); *A61K 39/39558* (2013.01);
(Continued)

(58) Field of Classification Search
None
See application file for complete search history.

(56) References Cited

U.S. PATENT DOCUMENTS 6,171,586 B1 * 1/2001 Lam ................. A61K 39/39591
424/130.1
7,635,570 B2  12/2009 Siena et al.
(Continued)

FOREIGN PATENT DOCUMENTS

KR   10-2008-0014745 A   2/2008
KR   10-2009-0101893 A   9/2009
(Continued)

OTHER PUBLICATIONS

Wang et al., Antibody structure, instability, and formulation, J. Pharm. Sci. 96:1-27, 2007.*

(Continued)

*Primary Examiner* — Claire Kaufman
(74) *Attorney, Agent, or Firm* — Sughrue Mion, PLLC

(57) ABSTRACT

The present invention provides a pharmaceutical formulation comprising an anti-epidermal growth factor receptor (EGFR) antibody. The pharmaceutical formulation has low turbidity, without showing aggregation or particle formation, even under accelerated conditions, and exhibits good stability. Therefore, the pharmaceutical formulation can be effectively used for the treatment of disorders such as cancer.

6 Claims, 35 Drawing Sheets

Specification includes a Sequence Listing.

(51) Int. Cl.
  *A61K 47/10* (2017.01)
  *A61K 47/12* (2006.01)
  *A61K 47/18* (2017.01)
  *A61K 47/26* (2006.01)
  *C07K 14/71* (2006.01)

(52) U.S. Cl.
  CPC .............. *A61K 47/10* (2013.01); *A61K 47/12* (2013.01); *A61K 47/183* (2013.01); *A61K 47/26* (2013.01); *C07K 16/2863* (2013.01); *C07K 2317/94* (2013.01)

(56) References Cited

U.S. PATENT DOCUMENTS

| | | | |
|---|---|---|---|
| 8,034,906 | B2 | 10/2011 | Borhani et al. |
| 8,748,175 | B2 * | 6/2014 | Kim .................. C07K 16/2863 435/358 |
| 2007/0087394 | A1 | 4/2007 | Siena et al. |
| 2010/0034823 | A1 | 2/2010 | Borhani et al. |
| 2011/0158987 | A1 | 6/2011 | Adler et al. |
| 2012/0231009 | A1 | 9/2012 | Ramani et al. |
| 2013/0216525 | A1 | 8/2013 | Chen |
| 2015/0071923 | A1 * | 3/2015 | Wei .................. A61K 47/6877 424/133.1 |
| 2015/0231220 | A1 * | 8/2015 | Kim .................. C07K 16/2863 424/185.1 |

FOREIGN PATENT DOCUMENTS

| | | |
|---|---|---|
| KR | 10-2012-0110175 A | 10/2012 |
| KR | 10-2013-0010898 A | 1/2013 |
| KR | 10-2013-0028894 A | 3/2013 |
| WO | 03009817 A2 | 2/2003 |
| WO | 2005058365 A1 | 6/2005 |
| WO | 2007147001 A2 | 12/2007 |
| WO | 2011080209 A2 | 7/2011 |
| WO | 2012138997 A1 | 10/2012 |
| WO | 2014096051 A1 | 6/2014 |
| WO | 2014177568 A1 | 11/2014 |

OTHER PUBLICATIONS

Bleeker et al., Dual mode of action of a human anti-epidermal growth factor receptor monoclonal antibody for cancer therapy, J. Immunol. 173:4699-4707, 2004.*

Normosol-R information sheet, Dailymed, National Library of Medicine. Retrieved online: URL<https://dailymed.nlm.nih.gov/dailymed/getFile.cfm?setid=c3335a21-20c9-46a5-5d9f-12227d67fd11&type=pdf&name=c3335a21-20c9-46a5-5d9f-12227d67fd11> (Retrieved on Jul. 16, 2019), 2009.*

Kim, S-H, EGFR targeting human mAb for cancer therapy, Retrieved online: <URL: http://ncc.ncc.re.kr/webzine/trend/trend/forum/39/1_1.pdf>, Retrieved Feb. 27, 2020, Apr. 25, 2013.*

Lee, K, How to gain a competitive advantage in the flood of antibodies and small molecules intercepting EGFR signal pathway? KASBP 2013 Fall Symposium Program, Retrieved onine: <URL: https://kasbp.org/resources/Documents/after%202013_KASBP_Fall_Program_FINAL-Full.pdf>. Retrieved Feb. 25, 2020, pp. 1-8 only, Nov. 2013.*

International Search Report of PCT/KR2016/000472, dated Jul. 25, 2016. [PCT/ISA/210].

Written Opinion of PCT/KR2016/000472, dated Jul. 25, 2016. [PCT/ISA/237].

Japan Patent Office, Communication dated May 29, 2018, issued in corresponding Japanese application No. 2017-537953.

European Patent Office, Communication dated May 9, 2018, issued in corresponding European application No. 16740356.7.

Japanese Patent Office; Communication dated Dec. 11, 2018, issued in counterpart Japanese application No. 2017-537953.

* cited by examiner

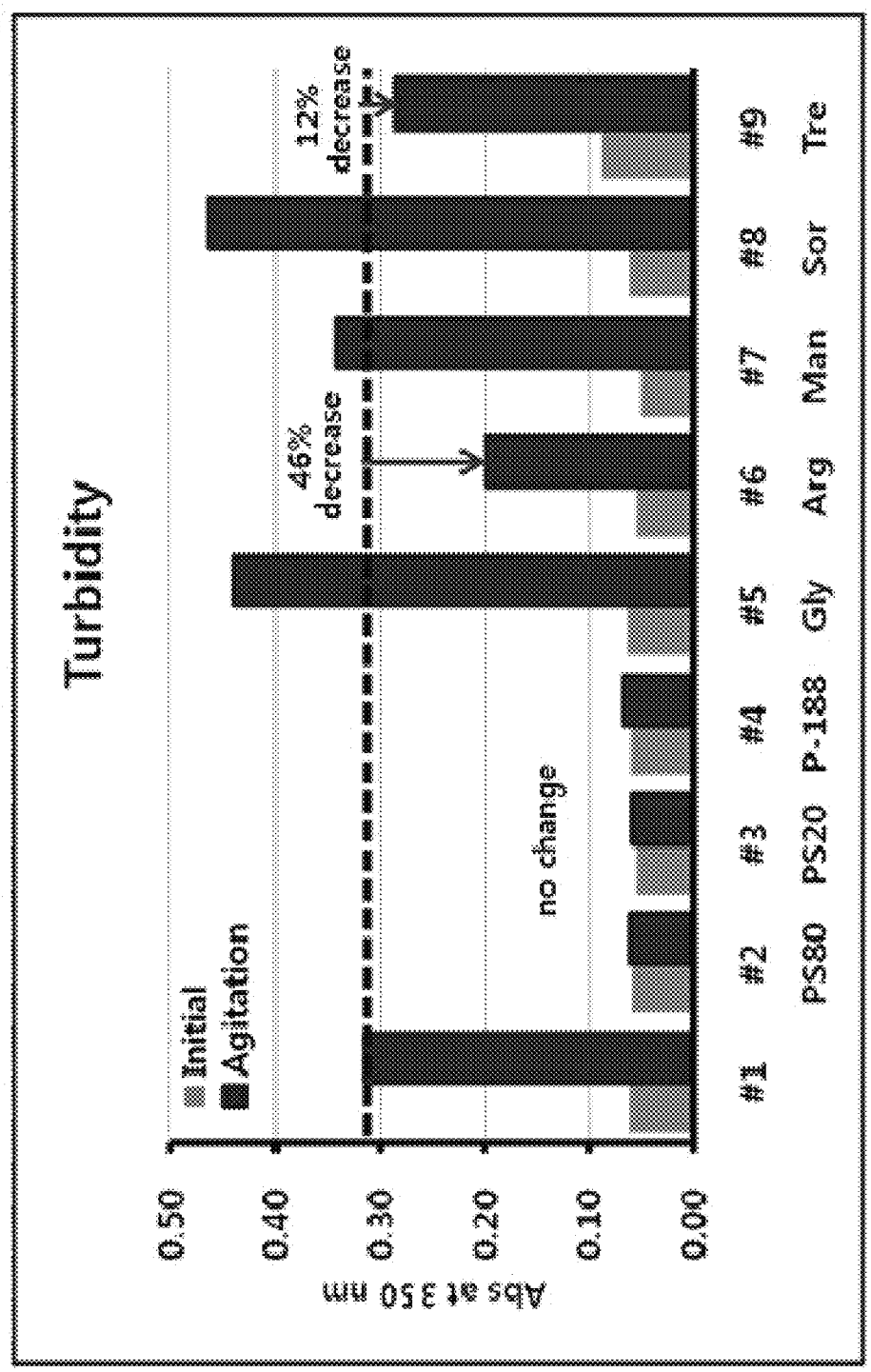

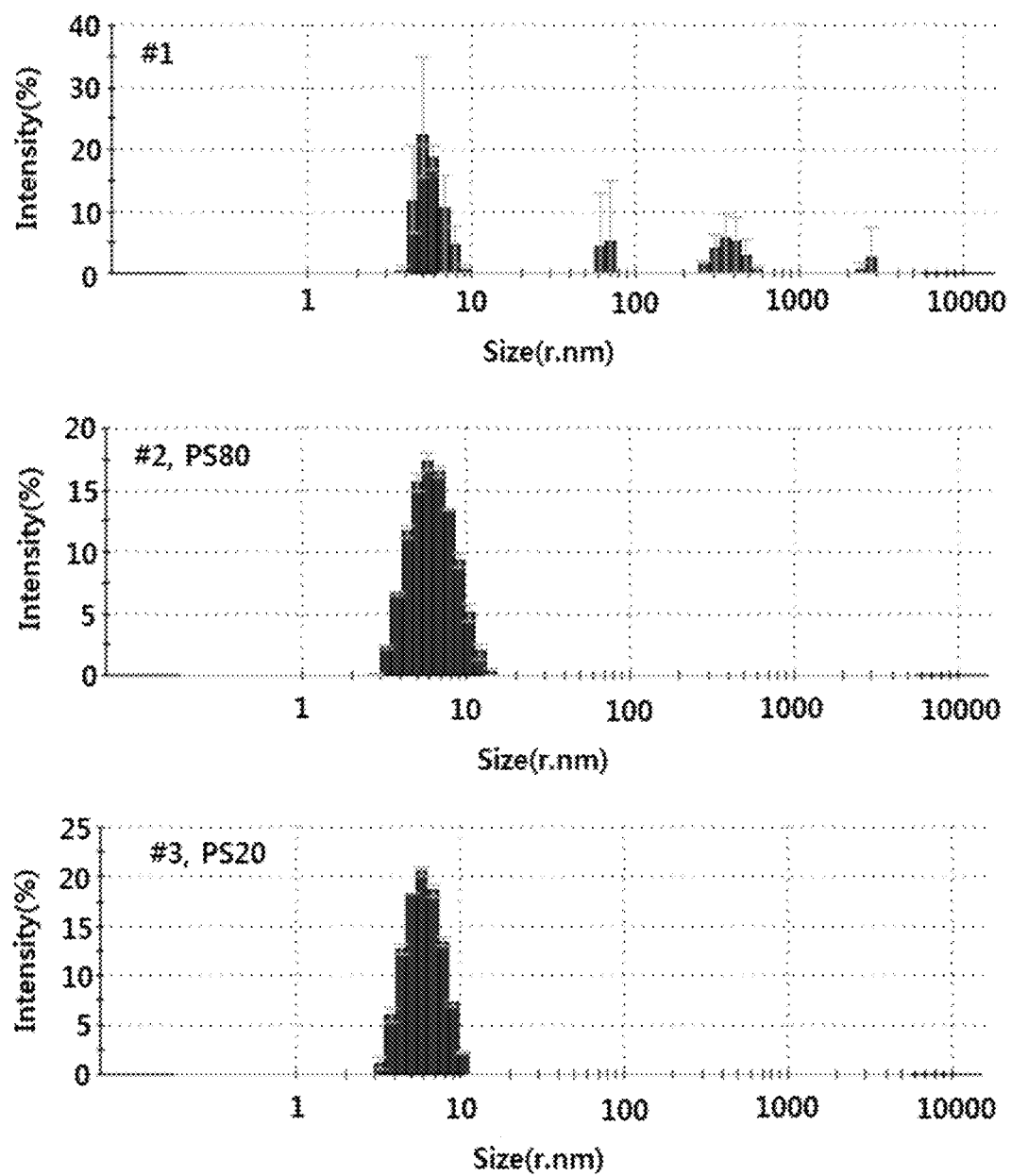

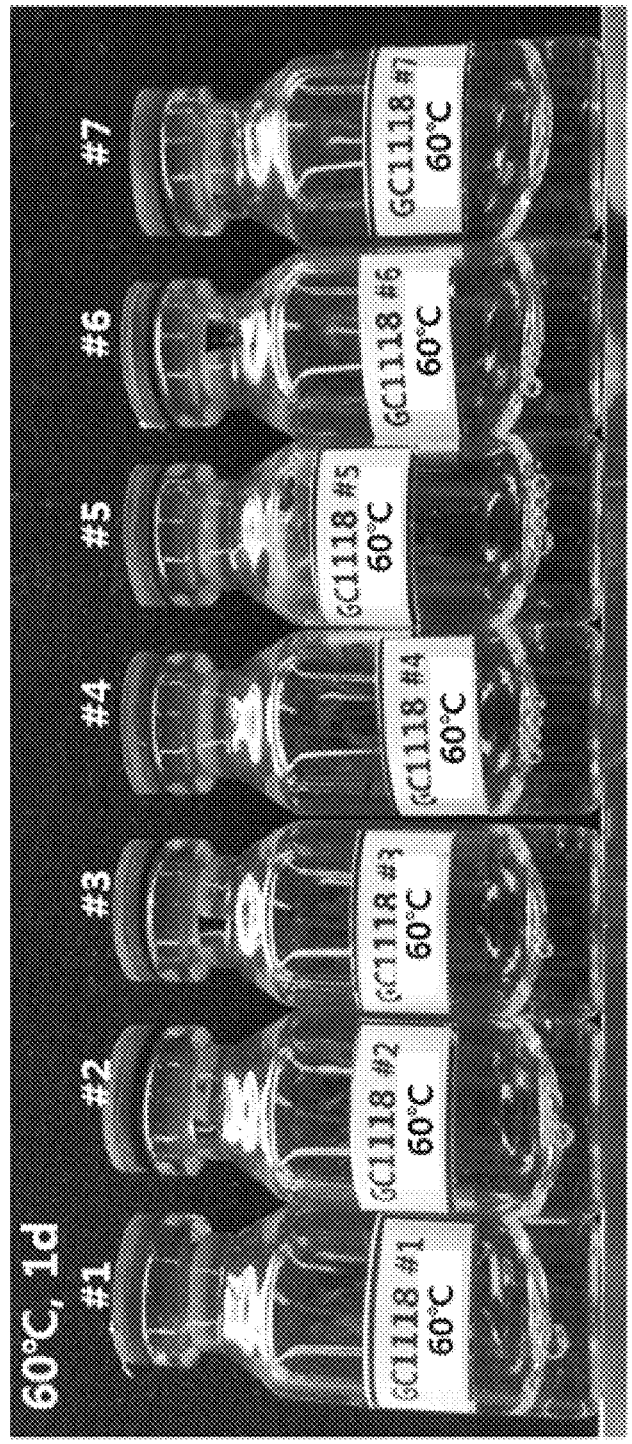

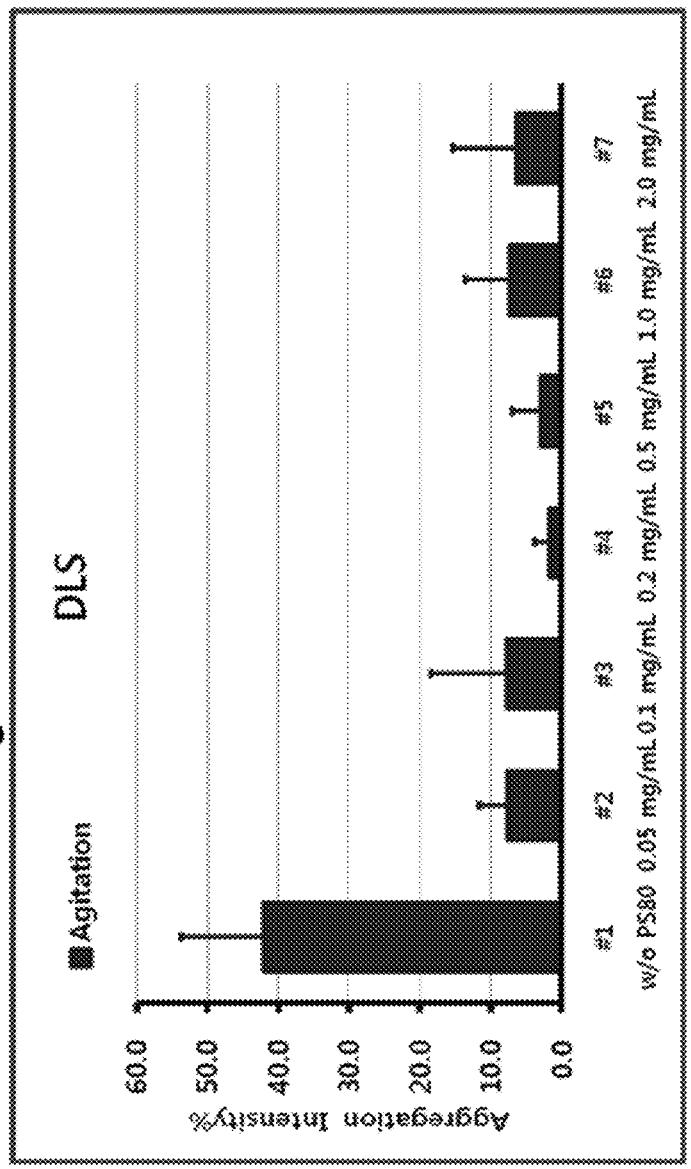

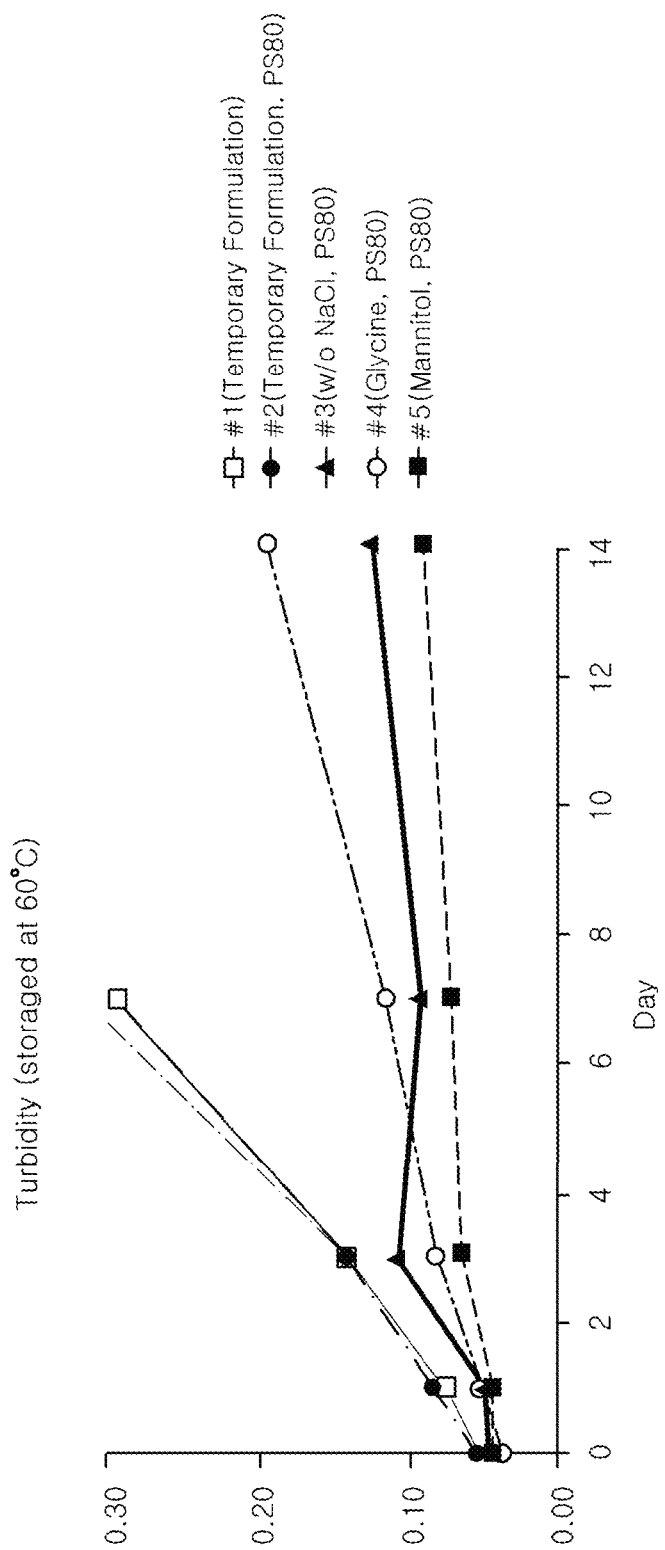

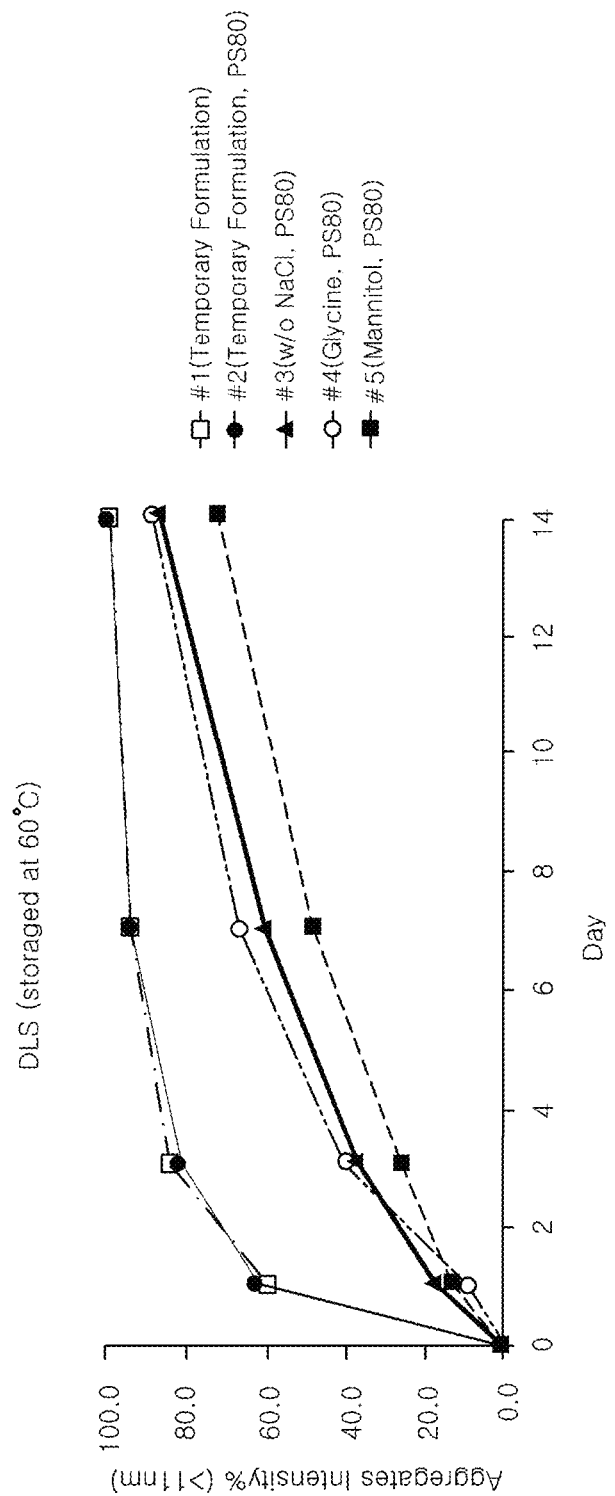

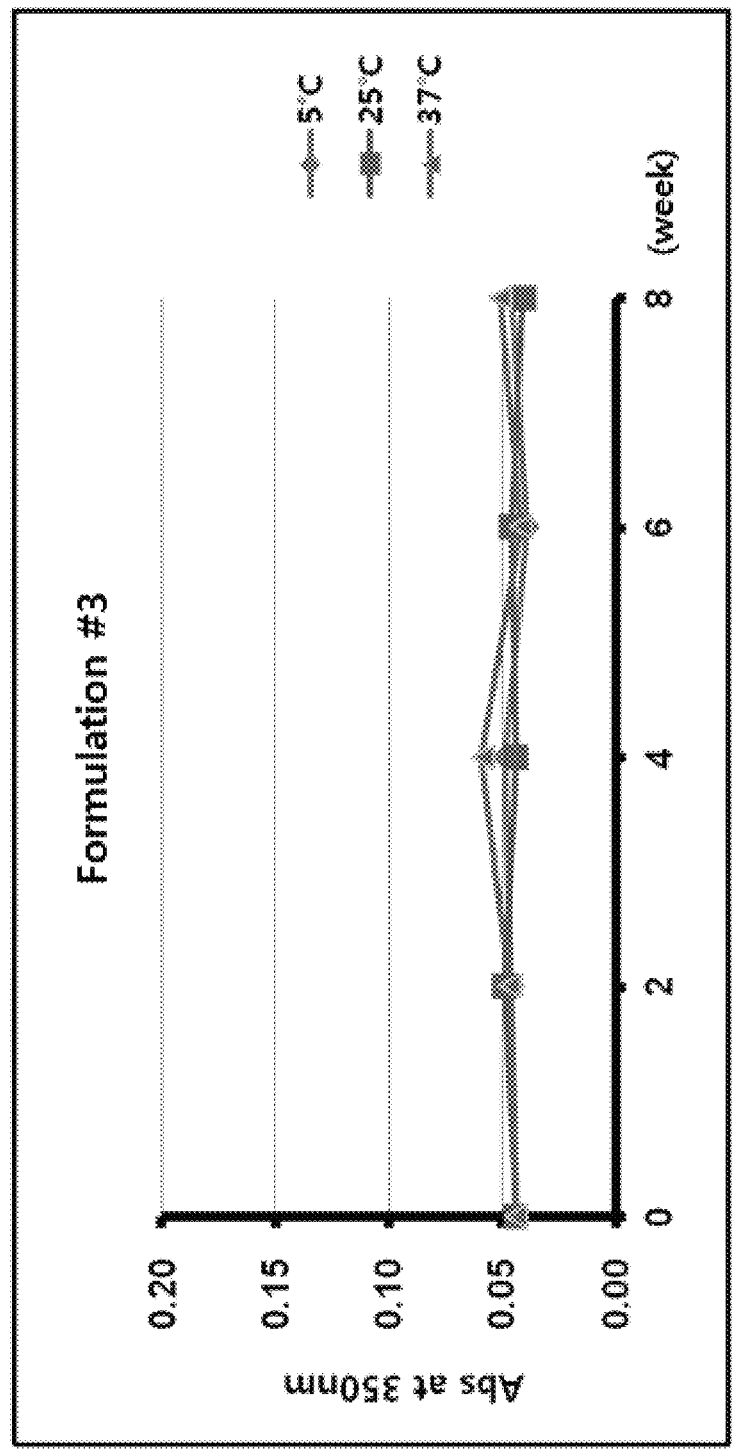

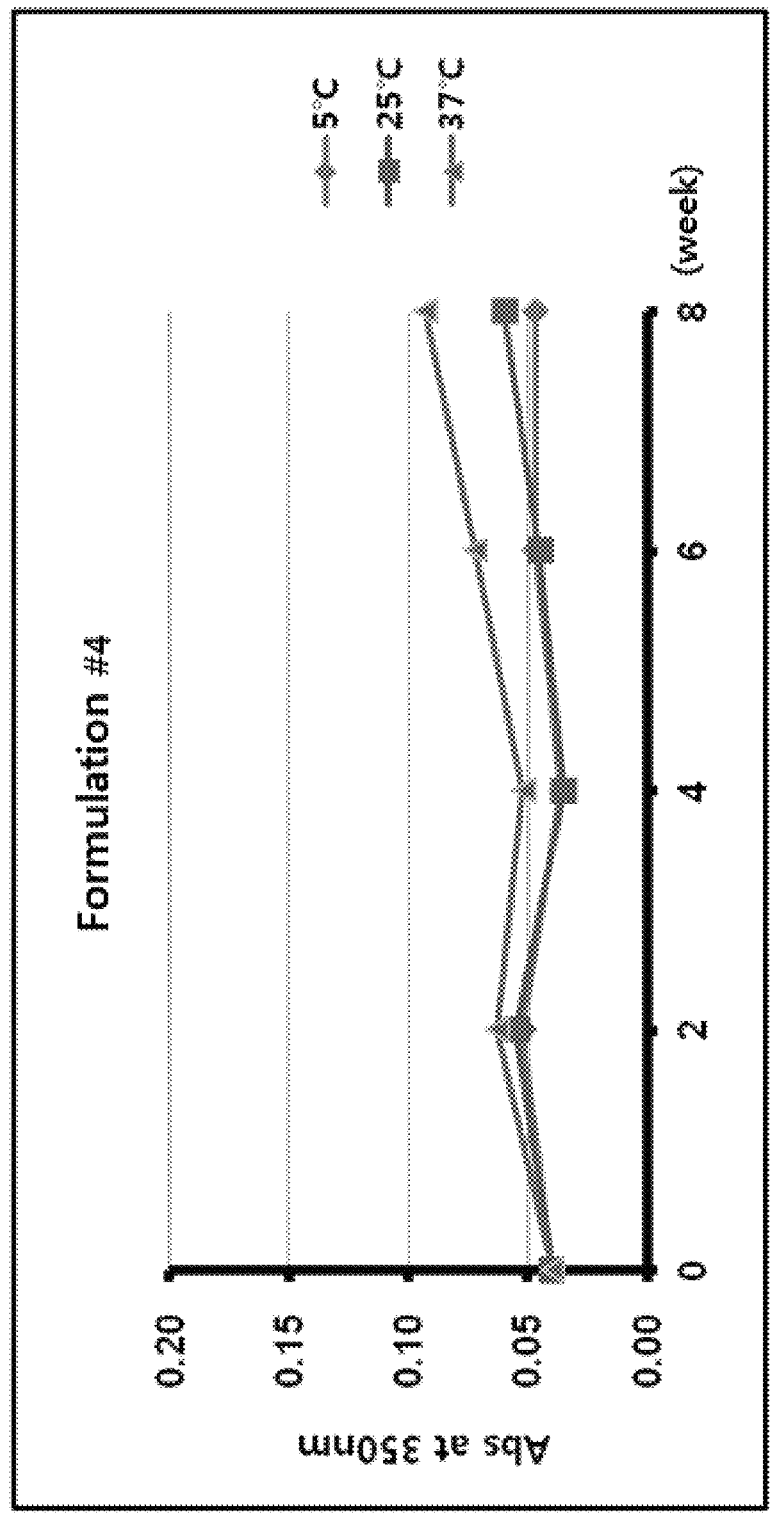

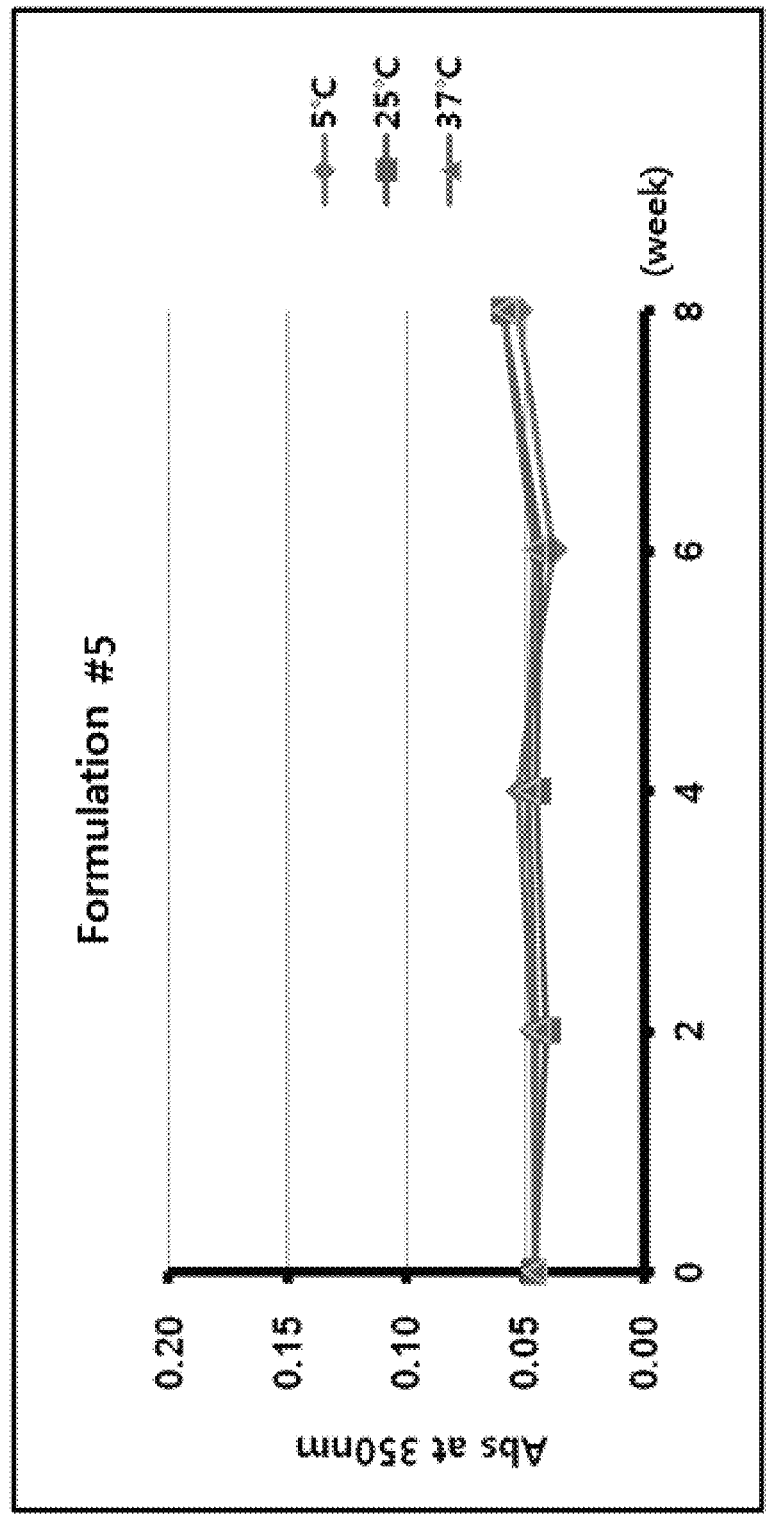

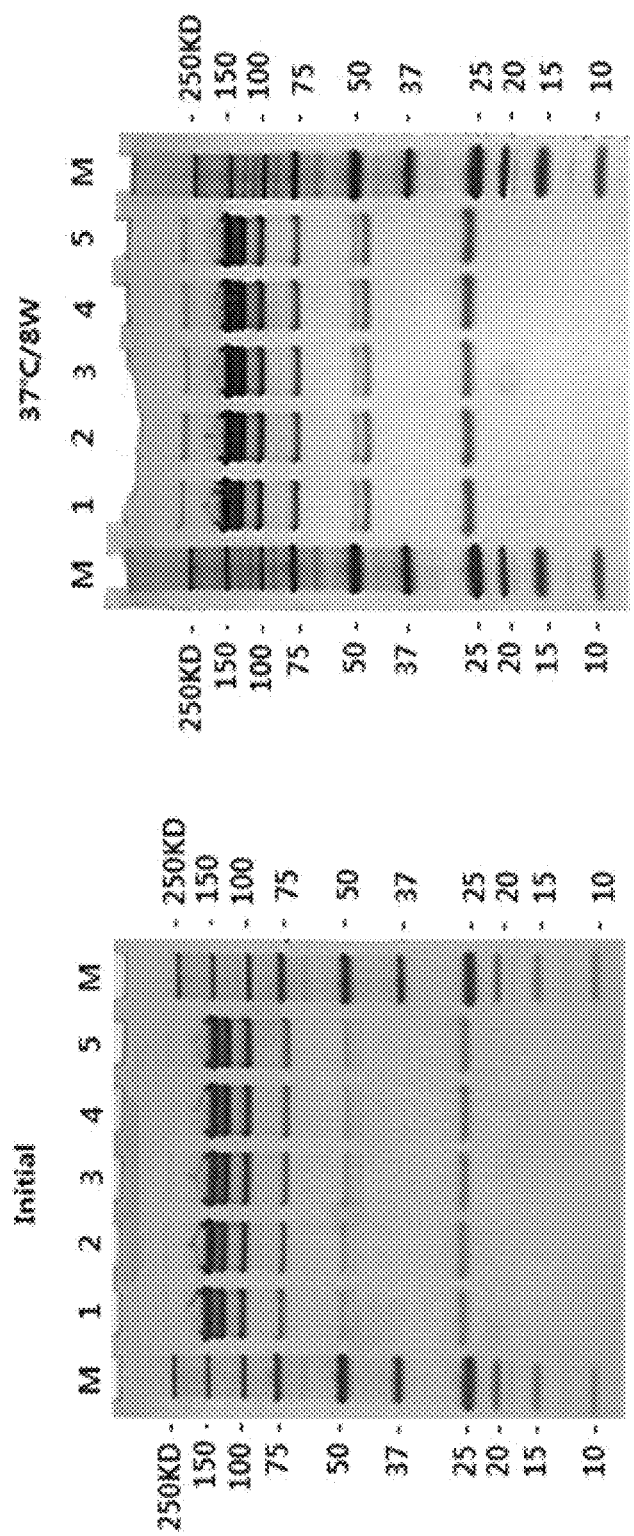

Fig. 10

Raw data

|  | Protein Concentration mg/mL (Initial) | Protein Concentration mg/mL (37°C/2W) | Protein Concentration (compared to Initial, %) |
|---|---|---|---|
| GC1118 #1 | 10.06 | 9.72 | 96.6 |
| GC1118 #2 | 10.02 | 10.00 | 99.8 |
| GC1118 #3 | 10.03 | 9.89 | 98.6 |
| GC1118 #4 | 9.95 | 9.75 | 97.9 |
| GC1118 #5 | 9.94 | 9.87 | 99.4 |
| GC1118 #6 | 9.97 | 9.84 | 98.7 |
| GC1118 #7 | 9.91 | 9.69 | 97.8 |
| GC1118 #8 | 9.75 | 9.84 | 101.0 |
| GC1118 #9 | 10.13 | 9.91 | 97.8 |
| GC1118 #10 | 9.91 | 9.62 | 97.1 |
| GC1118 #11 | 9.98 | 9.87 | 98.9 |
| GC1118 #12 | 9.97 | 9.81 | 98.4 |
| GC1118 #13 | 9.95 | 9.87 | 99.2 |
| GC1118 #14 | 9.97 | 9.80 | 98.3 |
| GC1118 #15 | 9.80 | 9.89 | 101.0 |
| GC1118 #16 | 9.80 | 10.00 | 102.1 |
| GC1118 #17 | 9.95 | 9.80 | 98.4 |
| GC1118 #18 | 9.94 | 9.86 | 99.2 |
| GC1118 #19 | 9.94 | 9.80 | 98.6 |
| GC1118 #20 | 9.97 | 9.84 | 98.7 |

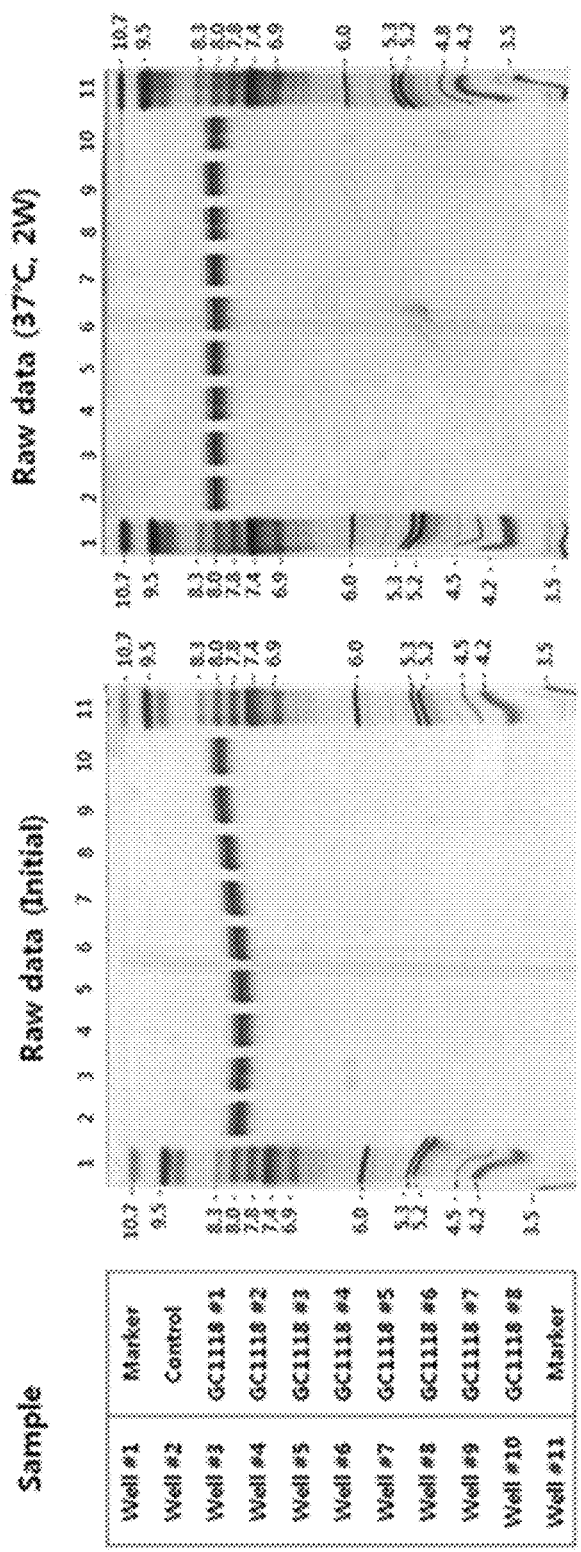

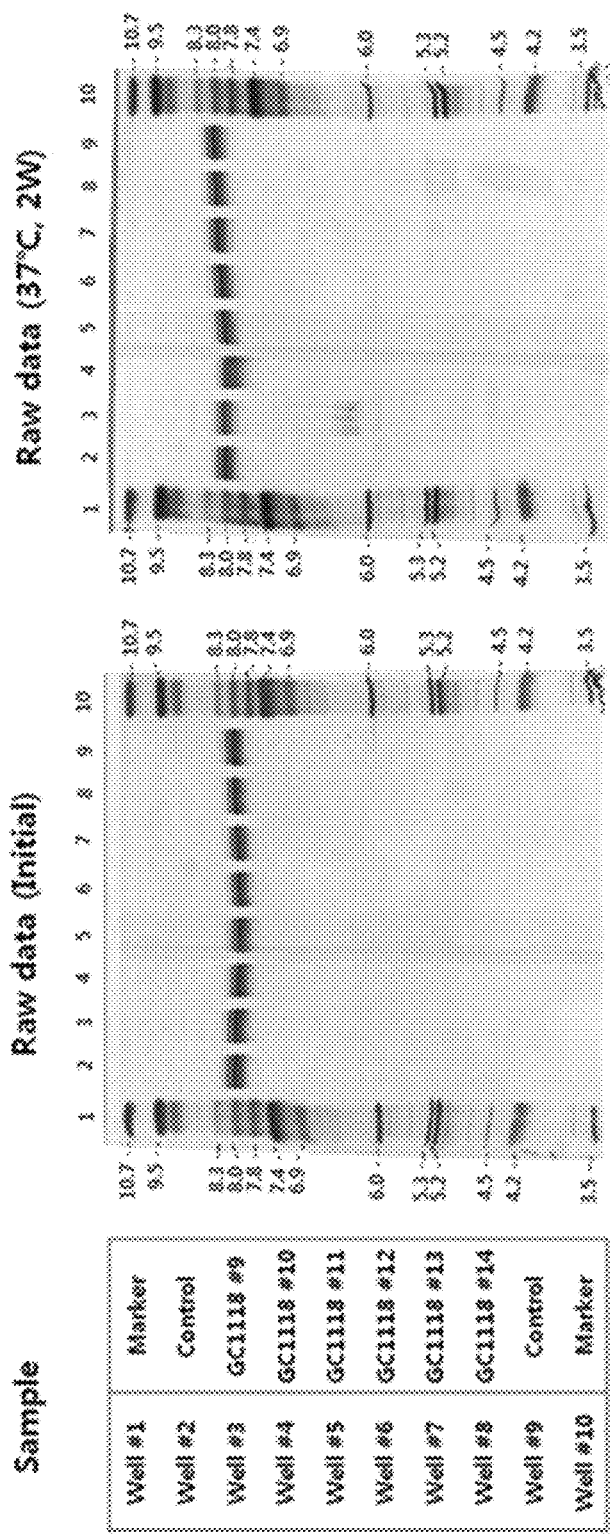

SEQUENCE LISTING

```
<160> NUMBER OF SEQ ID NOS: 3

<210> SEQ ID NO 1
<211> LENGTH: 219
<212> TYPE: PRT
<213> ORGANISM: artificial sequence
<220> FEATURE:
<223> OTHER INFORMATION: L chain of humanized antibody GC1118a
<300> PUBLICATION INFORMATION:
<301> AUTHORS: Lim et al.
<302> TITLE: GC1118, an Anti-EGFR Antibody with a Distinct Binding
      Epitope and Superior Inhibitory Activity against High-Affinity
      EGFR Ligands
<303> JOURNAL: Mol. Cancer Ther.
<304> VOLUME: 15
<305> ISSUE: 2
<306> PAGES: 251-263
<307> DATE: 2015-11-19
<308> DATABASE ACCESSION NUMBER: 4UV7_L
<309> DATABASE ENTRY DATE: 2016-03-02

<400> SEQUENCE: 1

Asp Ile Val Met Thr Gln Thr Pro Leu Ser Leu Pro Val Thr Pro Gly
1               5                   10                  15

Glu Pro Ala Ser Ile Ser Cys Arg Ser Asn Gln Asp Leu Thr His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60
```

Asp Arg Phe Ser Gly Ser Gly Ala Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Asn
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 225
<212> TYPE: PRT
<213> ORGANISM: artificial sequence
<220> FEATURE:
<223> OTHER INFORMATION: H chain of humanized antibody GC1118a
<300> PUBLICATION INFORMATION:
<301> AUTHORS: Lim et al.
<302> TITLE: GC1118, an Anti-EGFR Antibody with a Distinct Binding
      Epitope and Superior Inhibitory Activity against High-Affinity
      EGFR Ligands
<303> JOURNAL: Mol. Cancer Ther.
<304> VOLUME: 15
<305> ISSUE: 2
<306> PAGES: 251-263
<307> DATE: 2015-11-19
<308> DATABASE ACCESSION NUMBER: 4UV7_H
<309> DATABASE ENTRY DATE: 2016-03-02

<400> SEQUENCE: 2

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Ile Arg Gln Ala Pro Gly Lys Gly Leu Glu Trp Val
        35                  40                  45

Ser Gly Ile Leu Gly Ser Glu Arg Ser Tyr Tyr Arg Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Ser Pro Gly Tyr Thr Leu Tyr Ala Trp Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Lys Ala Glu Pro Lys Ser
            210                 215                 220

Cys
225

<210> SEQ ID NO 3
<211> LENGTH: 621
<212> TYPE: PRT
<213> ORGANISM: home sapiens
<300> PUBLICATION INFORMATION:
<301> AUTHORS: Lim et al.
<302> TITLE: GC1118, an Anti-EGFR Antibody with a Distinct Binding
      Epitope and Superior Inhibitory Activity against High-Affinity
      EGFR Ligands
<303> JOURNAL: Mol. Cancer Ther.
<304> VOLUME: 15
<305> ISSUE: 2
<306> PAGES: 261-263
<307> DATE: 2015-11-19
<308> DATABASE ACCESSION NUMBER: 4UV7_A
<309> DATABASE ENTRY DATE: 2016-03-02

<400> SEQUENCE: 3

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
                100                 105                 110

Met Arg Asn Leu Gln Glu Ile Leu His Gly Ala Val Arg Phe Ser Asn
            115                 120                 125

Asn Pro Ala Leu Cys Asn Val Glu Ser Ile Gln Trp Arg Asp Ile Val
        130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
            195                 200                 205

His Asn Gln Cys Ala Ala Gly Cys Thr Gly Pro Arg Glu Ser Asp Cys
        210                 215                 220
```

-continued

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
            405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
610                 615                 620

PHARMACEUTICAL FORMULATION COMPRISING ANTI-EGFR ANTIBODY

CROSS REFERENCE TO RELATED APPLICATIONS

This application is a National Stage of International Application No. PCT/KR2016/000472 filed Jan. 15, 2016, claiming priority based on Korean Patent Application No. 10-2015-0008677, filed Jan. 19, 2015, the contents of all of which are incorporated herein by reference in their entirety.

TECHNICAL FIELD

The present invention relates to a pharmaceutical formulation comprising an anti-EGFR antibody.

BACKGROUND ART

An antibody binding to epidermal growth factor receptor (EGFR) is called an anti-EGFR antibody. Examples of such antibody include cetuximab which is a chimeric antibody containing a variable region of mouse origin and a constant region of human origin (Naramura et al., *Cancer Immunol. Immunotherapy,* 1993, 37: 343-349, and International Publication NO. WO 96/40210), and MAB 425 which is an original mouse antibody to EGFR (Kettleborough et al., *Protein Engineering,* 1991, 4: 773-783).

According to various in vitro and in vivo study results on the anti-EGFR antibody, the anti-EGFR antibody inhibits cancer cell proliferation, reduces tumor-mediated angiogenesis, induces cancer cell apoptosis, and enhances the toxic effects of radiation therapy and traditional chemotherapy. As such, the anti-EGFR antibody can suppress tumors at various levels.

However, a liquid formulation comprising an anti-EGFR antibody for a therapeutic purpose may have problems in that protein multimers may be formed due to the aggregation property of the antibodies, and a deamination reaction may also take place due to proteolytic reactions. Such denaturation reaction may be caused by, for example, storing at an elevated temperature during transportation or a shear stress. If a liquid formulation comprising the anti-EGFR antibody shows aggregation due to denaturizaiton reactions, a precipitation and the formation of particles may take place, which may induce embolism.

In this regard, the liquid formulation may be subjected to filtration process before administration to a patient (e.g., injection by a syringe) in order to prevent aggregation. However, such additional step may render the administration method complicated and unsuitable for a clinical test. Also, the particle formation may continue to take place ever after the filtration process, leading to a decrease in stability.

Therefore, there has been a persistent need to develop a stable pharmaceutical formulation comprising an anti-EGFR antibody which has low turbidity, without showing aggregation or particle formation, even under a stress condition.

Meanwhile, a conventional pharmaceutical formulation comprising an anti-EGFR antibody normally comprises sodium chloride (NaCl) as an isotonization agent in order to reduce a pain reaction in the body caused by the osmotic pressure when the pharmaceutical formulation is administered. However, a pharmaceutical formulation comprising a protein therapeutics should contain appropriate ingredients which are suitable therefor. In this regard, the compatibility of NaCl should be also verified.

DISCLOSURE OF INVENTION

Technical Problem

An object of the present invention is to provide a pharmaceutical formulation comprising an anti-EGFR antibody which shows excellent stability.

Solution to Problem

The present invention provides a pharmaceutical formulation containing an anti-EGFR antibody, sodium acetate anhydrous, and polysorbate 80, which does not contain any sodium chloride (NaCl).

Advantageous Effects of Invention

Since a pharmaceutical formulation comprising an anti-EGFR antibody according to the present invention does not contain sodium chloride, unlike most of the conventional pharmaceutical formulations comprising an anti-EGFR antibody which contains sodium chloride, such pharmaceutical formulation has low turbidity, without showing aggregation or particle formation, even under accelerated conditions, and exhibits good stability. Therefore, the present pharmaceutical formulation can be effectively used for the treatment of cancer and the like.

BRIEF DESCRIPTION OF DRAWINGS

FIGS. 1A, 1B and 1C respectively show the results of visual inspection, turbidity, and dynamic light scattering (DLS) analysis using the samples prepared for the selection of the type of a surfactant and a tonicifier.

FIGS. 4A, 4B and 4C respectively show the results of visual inspection, turbidity, and DLS analysis using the samples prepared for the screening of the type of a tonicifier.

FIGS. 5A, 5B and 5C respectively show the results of visual inspection, turbidity, and DLS analysis using the samples prepared for the determination of the concentration of polysorbate 80.

FIGS. 6A and 6B respectively show the results of turbidity and DLS analysis after storage at a high temperature using the pharmaceutical formulations of Preparation Examples and Comparative Preparation Examples.

FIGS. 7A, 7B and 7C respectively show the results of turbidity changes of Preparation Examples 1 to 3 (formulations 3 to 5) at different temperatures.

FIGS. 8A and 8B respectively show the SDS-PAGE results of the pharmaceutical formulations of Preparation Examples and Comparative Preparation Examples stored at 37° C., under non-reducing and reducing conditions.

FIGS. 9, 10, 11, 12, 13A, 13B, 13C and 14 respectively show the results of visual inspection, protein concentration, SE-HPLC, IE-HPLC, IEF (Isoelectric focusing) and SDS-PAGE analysis of each sample prepared by Response Surface Methodology (RSM) design under the storage condition of 37° C. for two weeks.

BEST MODE FOR CARRYING OUT THE INVENTION

Figure 1A:

The present invention provides a liquid pharmaceutical formulation containing an anti-EGFR antibody, sodium acetate anhydrous, and polysorbate 80, which does not contain sodium chloride (NaCl).

The pharmaceutical formulation of the present invention may be preferably in the form of a liquid formulation in consideration of the user's convenience.

The pharmaceutical formulation of the present invention is characterized in that it contains no NaCl.

Generally, pharmaceutical formulations containing an anti-EGFR antibody comprise NaCl as tonicity modifier in order to reduce a pain reaction in the body caused by the osmotic pressure when the pharmaceutical formulation is administered. However, unlike conventional pharmaceutical formulations, NaCl is not comprised in the pharmaceutical formulations of the present invention so as to prepare a more stable pharmaceutical formulation comprising an anti-EGFR antibody which has low turbidity, without showing aggregation or particle formation, even under accelerated conditions. It is preferred that no NaCl is included in the anti-EGFR antibody formulation of the present invention, considering the compatibility with NaCl, which leads to minimal aggregation and particle formation, allowing the distribution of more stable products.

In one embodiment of the present invention, the main factors influencing turbidity, aggregation and particle formation of an antibody formulation were examined. The main factors influencing turbidity were found to be NaCl, the concentration of buffering agent and pH (FIG. 2A); and according to DLS analysis, the main factors influencing the reduction of the monomer intensity were found to be pH and NaCl (FIG. 2B). Further, according to SE-HPLC analysis, the main factors influencing the main peak reduction were found to be pH and NaCl (FIG. 3A); and according to IE-HPLC analysis, the main factors influencing the main peak reduction were pH and the concentration of buffering agent (FIG. 3B).

Based on these results, it is preferred that an antibody formulation should not contain NaCl so as to reduce turbidity and inhibit aggregation and particle formation.

The pharmaceutical formulation of the present invention contains an anti-EGFR antibody.

The anti-EGFR antibody can be comprised in a concentration of 1 to 16 mg/ml, preferably 2 to 10 mg/ml (for example, 10 mg/ml).

The anti-EGFR antibody for use in the present invention may be a conventional anti-EGFR antibody already known or commercially available. For example, an anti-EGFR antibody disclosed in U.S. Pat. No. 6,217,866 or Korean Patent No. 1108642 can be used.

The pharmaceutical formulation of the present invention contains sodium acetate anhydrous as a buffering agent.

According to one embodiment of the present invention, the main factors influencing turbidity, aggregation and particle formation include the concentration of buffering agent and pH. Therefore, the type of buffering agent, and its concentration and pH are important factors.

Sodium acetate anhydrous is used to maintain the pH of a pharmaceutical formulation of the present invention, which minimizes the pH changes due to external influences.

Sodium acetate anhydrous can be replaced with a buffering agent selected from the group consisting of sodium phosphate, glutamate, histidine, and a combination thereof. However, in order to reduce turbidity and inhibit aggregation and particle formation in the pharmaceutical formulation, appropriate range of pH should be selected. According to the present invention, in or around the pH range of 5 to 6, it is preferred to use sodium acetate anhydrous as a buffering agent.

Sodium acetate anhydrous can be included in a concentration of 10 to 200 mM, preferably 10 to 100 mM (for example, 50 mM).

A pharmaceutical formulation of the present invention can have a pH ranging from 5 to 7, preferably 5.3 to 6.1.

The pharmaceutical formulation of the present invention contains polysorbate 80 as a surfactant.

Generally, a solution containing an antibody has a high surface tension in the air-water interface. To reduce such surface tension, antibodies have a tendency to aggregate in the air-water interface. By minimizing the antibody aggregation in the air-water interface, a surfactant helps maintain the biological activity of the antibodies in the solution.

According to one embodiment of the present invention, a mechanical stress test of an antibody formulation containing polysorbate 80, polysorbate 20 or poloxamer 188 as a surfactant was carried out. As a result, it was found that it is preferable to contain polysorbate 80 to achieve the effects of reducing turbidity and inhibiting aggregation and particle formation of the pharmaceutical formulation (see Example 1).

In addition, according to another embodiment of the present invention, with respect to an antibody formulation containing various concentration of polysorbate 80, an antibody formulation containing polysorbate 80 in a concentration of 0.05 to 2.0 mg/ml was found to have the effects of reducing turbidity and inhibiting aggregation and particle formation. In particular, the degree of aggregation and particle formation was found to be the least when polysorbate 80 was comprised in a concentration of 0.2 mg/ml (see Example 4).

Therefore, polysorbate 80 can be comprised in a concentration of 0.05 to 2.0 mg/ml, preferably 0.1 to 1.0 mg/ml (for example, 0.2 mg/ml).

The pharmaceutical formulation of the present invention can further contain a tonicifier.

A tonicifier in the present invention plays a role of inhibiting the aggregation and degradation of the pharmaceutical formulation.

In particular, it is preferable to employ mannitol, glycine or a combination thereof as a tonicifier, so as to reduce turbidity and inhibit aggregation and particle formation. According to one embodiment of the present invention, it was found that an antibody formulation containing mannitol or glycine as a tonicifier can significantly inhibit turbidity increase (see Example 3).

The tonicifier may be mannitol, which can be comprised in a concentration of 1 to 20% (w/v), preferably 2 to 10% (w/v), for example, 5% (w/v).

The tonicifier may be glycine, which can be comprised in a concentration of 1 to 10% (w/v), preferably 2 to 5% (w/v), for example, 3% (w/v).

The tonicifier may be a combination of mannitol and glycine wherein mannitol and glycine are mixed in a weight ratio of 5:1 to 1:5, which can be comprised in a concentration of 1 to 10% (w/v), preferably 2 to 5% (w/v).

One embodiment of the present invention provides a pharmaceutical formulation consisting of 10 mg/ml of an anti-EGFR antibody, 50 mM of sodium acetate anhydrous and 0.2 mg/ml of polysorbate 80, which does not contain NaCl.

Another embodiment of the present invention provides a pharmaceutical formulation consisting of 10 mg/ml of an anti-EGFR antibody, 50 mM of sodium acetate anhydrous, 0.2 mg/ml of polysorbate 80 and 5% (w/v) of mannitol, which does not contain NaCl.

A further embodiment of the present invention provides a pharmaceutical formulation consisting of 10 mg/ml of an anti-EGFR antibody, 50 mM of sodium acetate anhydrous, 0.2 mg/ml of polysorbate 80 and 3% (w/v) of glycine, which does not contain NaCl.

According to the stability analysis results examined under stress conditions, the pharmaceutical formulations of the present invention maintained colorless and transparent state, showing low rate of turbidity increase; and did not exhibit aggregations even after a long-term storage, maintaining good purity, as compared to a pharmaceutical formulation containing NaCl. Based on these results, it was found that a pharmaceutical formulation containing an anti-EGFR antibody has superior stability when no NaCl is included (see Test Examples).

A pharmaceutical formulation according to the present invention can further contain pharmaceutically acceptable additives such as a diluent, a carrier, a stabilizer, an antioxidant, a preservative, etc., if necessary.

The diluent can be a saline, glucose, Ringer or an aqueous buffer solution. The carrier can be a buffered saline solution, ethanol, polyol (e.g., glycerol, propylene glycol and liquid polyethylene glycol) and the like. The stabilizer can be an amino acid, cyclodextrin, polyethylene glycol, albumin (e.g., human serum albumin (HSA) and bovine serum albumin (BSA)), a salt (e.g., sodium chloride, magnesium chloride and calcium chloride), a chelator (e.g., EDTA) and the like. The antioxidant can be ascorbic acid, glutathione and the like. The preservative can be phenol, m-cresol, methyl- or propylparaben, chlorobutanol, benzalkonium chloride and the like.

A pharmaceutical formulation according to the present invention can be administered in various ways known in the art, for example, oral or parenteral administration. Examples of the parenteral administration may include intravenous, intramuscular, intraarterial, intramembraneous, intracapsular, intraorbital, intracardiac, intradermal, intraperitoneal, via bronchoscopy, subcutaneous, intra-subcutaneous layer, intraarticular, subcapsular, subarachnoidal, intrathecal, epidural and intrasternal injection and infusion, but are not limited thereto.

The daily dosage of a pharmaceutical formulation of the present invention may range from 0.01 to 10 mg/kg (body weight), preferably 0.01 to 1.0 mg/kg body weight, and it can be administered once or in divided doses per day. However, the actual dose of the pharmaceutical formulation should be determined in consideration of various relevant factors such as the route of administration, age, sex, weight, disease severity, etc., and thus, the above dosage does not limit the scope of the present invention in any way.

EXAMPLES

Hereinafter, the present invention is explained in detail by Examples. The following Examples are intended to further illustrate the present invention without limiting its scope.

The providers of the reagents used in the Examples below are as follows.

Reagents and Test Solutions

Sodium acetate anhydrous (Scharlau, Cat. No. SO0032)
Sodium phosphate monobasic (Scharlau, Cat. No. SO0333)
Sodium phosphate dibasic (JT Baker, Cat. No. 3817-05)
Polysorbate 20 (Tween 20, Merck, Cat. No. 8.17072.1000)
Polysorbate 80 (Tween 80, Fluka, Cat. No. 59924)
Poloxamer 188 (Pluronic F68, Sigma, Cat. No. P-1300)
NaCl (Scharlau, Cat. No. SO0225)
Mannitol (JT Baker, Cat. No. 238506)
Sorbitol (Sigma, Cat. No. S7547)
Glycine (Sigma, Cat. No. 15527)
Trehalose dihydrate (Sigma, Cat. No. T5251)
Arginine hydrochloride (Arg-HCl, Scharlau, Cat. No. AR0125)

The samples in the Examples below were prepared by mixing the ingredients according to each design condition, filtering them through a 0.22 μm filter, subdividing them into 3 ml glass vials in a clean bench, and stoppering them with a rubber plug, which were stored for use in the experiments.

Test methods used in the present invention are as follows.

(1) Mechanical stress: A vial was fixed in a vortex mixer (Vortex-Genie 2, Scientific Industries) and vortexed at 3000 rpm at room temperature for 4 hours.

(2) Thermal stress: A vial was put into a 37° C. thermohygrostat (LHD-2250C, Labtech) or 60° C. thermostat (DX7, Hanyoung).

(3) Visual inspection: Aggregation formation was observed with naked eyes.

(4) Turbidity: After preparing 1 mL of each sample solution without dilution, the absorbance was measured using a UV spectrophotometer (LibraS32, Biochem) at 350 nm, to analyze turbidity.

(5) Dynamic light scattering (DLS): After preparing at least 1 mL of each sample solution without dilution, the size distribution chart of the sample solution was analyzed using a DLS instrument (Zetasizer Nano ZS90, Malvern Instrument).

(6) SDS-PAGE: Analysis was carried out by a conventional SDS-PAGE analysis method using an electrophoresis device.

(7) Isoelectric focusing (IEF): Analysis was carried out by a conventional IEF analysis method using an electrophoresis device.

(8) UV protein quantitation: Absorbance was measured using a spectrophotometer at 280 nm and protein quantitation analysis was carried out.

(9) SE-HPLC: Analysis was carried out by using SE-HPLC analytical column (TSK gel G3000SW$_{XL}$, Cat. No. 08541, Tosoh Corporation).

(10) IE-HPLC: Analysis was carried out by using IE-HPLC analytical column (Propac WCX-10 analytical, Cat. No. 054993, Dionex).

(11) Potency 1 (Binding assay): ELISA reader (Spectra Max 190, Molecular Devices) was used for potency 1 analysis.

(12) Potency 2 (Cell based assay): The identical number of cells calculated by cell counting were aliquoted into each well of a 96-well plate. After culturing them for 24 hours, culture medium was removed. Then, 100 μL of diluted sample solution was put into each well. And 100 μL of diluted standard substance and diluted sample were put into each well and cultured for 5 days. 40 μL of MTS reagent was put into each well and was wrapped by a foil and reacted at 37° C. for 3 hours. The absorbance was measured at 490 nm using ELISA reader (Spectra Max 190, Molecular Devices).

<Screening for the Preparation of Optimized Antibody Formulation>

Example 1: Selection of Type of Surfactant and Tonicifier

To select the type of surfactant and tonicifier which can inhibit aggregation and particle formation, each sample was prepared by mixing the ingredients as shown in Table 1.

TABLE 1

| No | Buffer | pH | Surfactant | Tonicifier |
|---|---|---|---|---|
| 1 | 50 mM Na-Acetate | 5.8 | — | 110 mM NaCl |
| 2 | 50 mM Na-Acetate | 5.8 | 2 mg/ml PS80 | 110 mM NaCl |
| 3 | 50 mM Na-Acetate | 5.8 | 2 mg/ml PS20 | 110 mM NaCl |
| 4 | 50 mM Na-Acetate | 5.8 | 2 mg/ml P-188 | 110 mM NaCl |
| 5 | 50 mM Na-Acetate | 5.8 | — | 110 mM NaCl/ 3% Gly |
| 6 | 50 mM Na-Acetate | 5.8 | — | 110 mM NaCl/ 3% Arg-HCl |
| 7 | 50 mM Na-Acetate | 5.8 | — | 110 mM NaCl/ 6% Mannitol |
| 8 | 50 mM Na-Acetate | 5.8 | — | 110 mM NaCl/ 6% Sorbitol |
| 9 | 50 mM Na-Acetate | 5.8 | — | 110 mM NaCl/ 6% Trehalose |

Figure 1C:
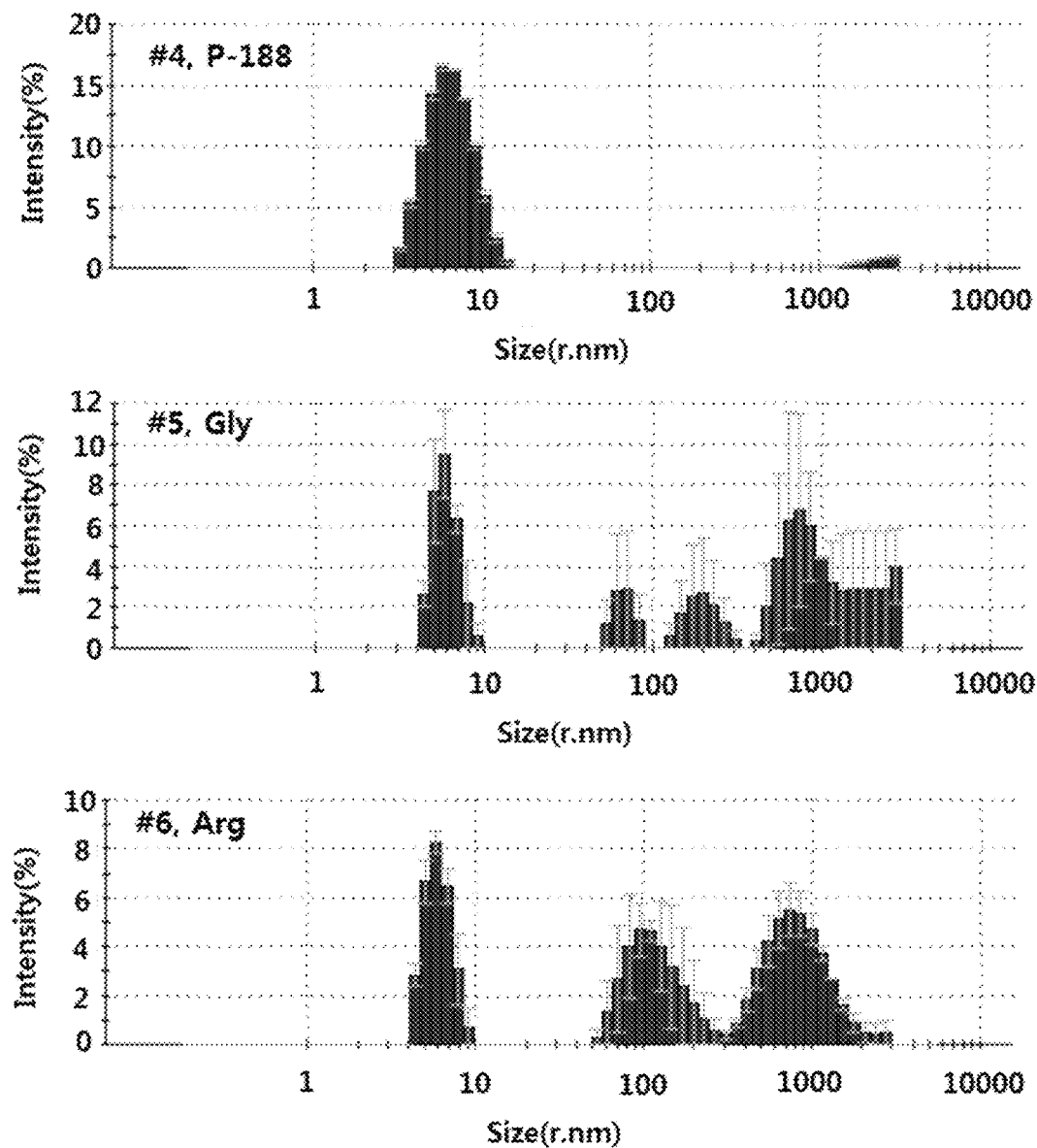

A mechanical stress test was performed with the samples prepared above, and the results of visual inspection, turbidity, and DLS analysis are shown in FIGS. 1A, 1B, and 1C, respectively.

Figure 1C:
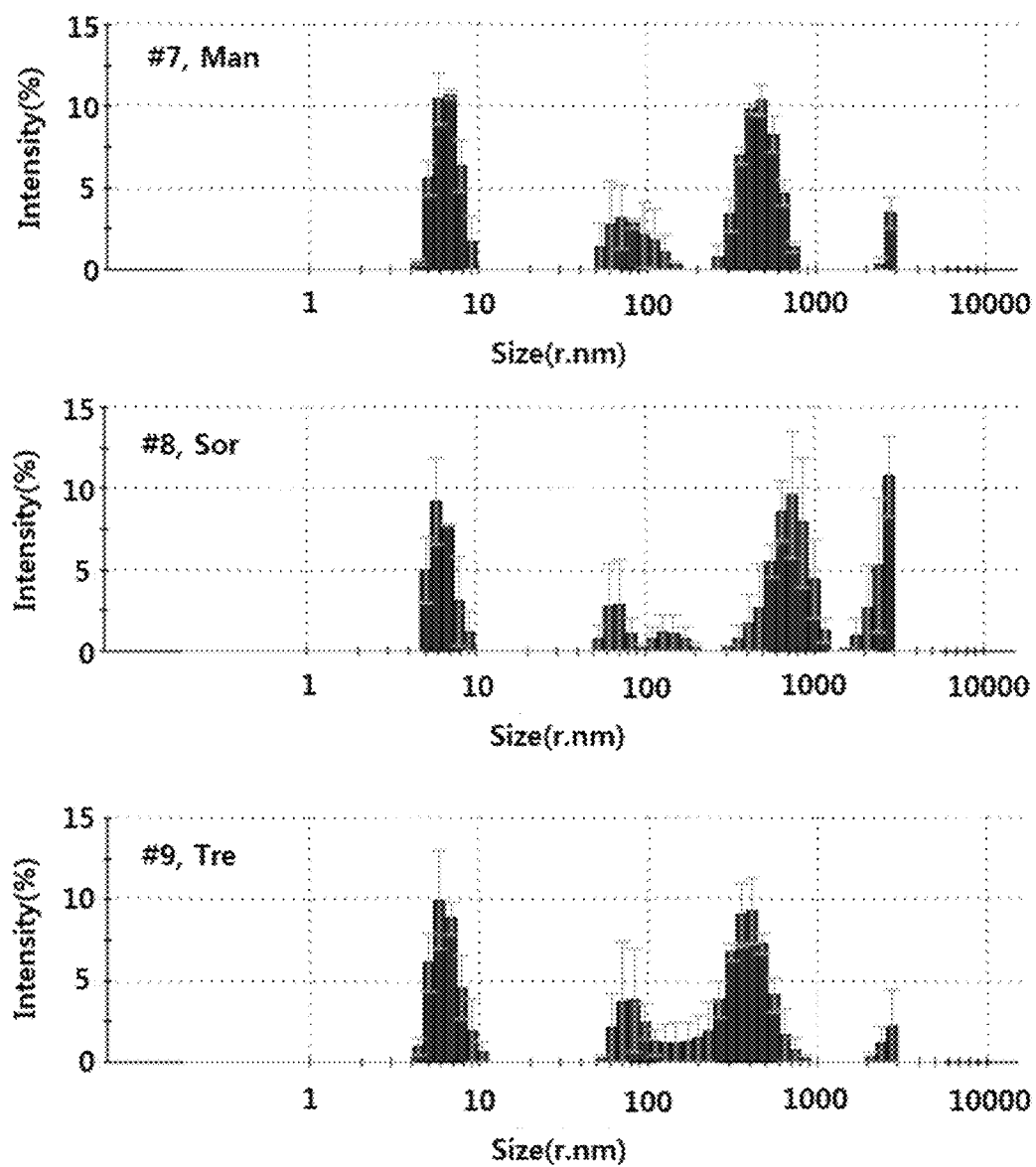

As shown in FIG. 1, turbidity determined by visual inspection was in the order of #1, #5, #8>#7, #9>#6>#2, #3, #4. And, the measurement of turbidity of the samples revealed the following results: the samples with a surfactant didn't show turbidity increase; and the samples with an additional tonicifier showed turbidity decrease. More particularly, Arg-HCl-added sample (#6) showed 46% decrease, and trehalose-added sample (#9) showed 12% decrease in turbidity as compared to sample #1. DLS analysis revealed that a surfactant inhibited aggregation formation, while a tonicifier increased aggregation intensity.

Therefore, with regard to a surfactant (considering turbidity, aggregation formation and other competing drug formulations), polysorbate 80 (PS80) was preferred over polysorbate 20 (PS20) or poloxamer 188 (P-188); and with regard to a tonicifier, Arg-HCl was preferred, in terms of turbidity.

Example 2: Selection of Factors for Aggregation and Particle Formation

To identify the main factors influencing aggregation and particle formation in a pharmaceutical formulation containing an anti-EGFR antibody (GC1118A, Mogam Biotechnology Institute), each sample was prepared by mixing the ingredients as shown in Table 2.

The anti-EGFR antibody GC1118A in a complex with extracellular domain of EGFR is described in Lim et al., GC1118, an Anti-EGFR Antibody With a Distinct Binding Epitope and Superior Inhibitory Activity Against High-Affinity EGFR Ligands, Mol. Cancer, Ther. 15(2), 251–263, February 2016 (e-publication Nov. 19, 2015) and deposited at the National Center for Biotechnology Information (NCBI) under accession number 4UV7 (www.ncbi.nim.nih-.gov/Structure/pdb/4UV7). Sequence of light chain of GC1118A is available under ID 4UV7_L (SEQ ID NO: 1), heavy chain of GC1118A is available under ID 4UV7_H (SEQ ID NO: 2), and chain A of EGFR is available under ID 4UV7_A (SEQ ID NO: 3).

TABLE 2

| No | Protein concentration (mg/ml) | Buffer | pH | Surfactant | Tonicifier |
|---|---|---|---|---|---|
| 1 | 2 | 10 mM Na-Acetate | 4 | — | — |
| 2 | 2 | 10 mM Na-Phosphate | 8 | 2 mg/ml PS80 | — |
| 3 | 2 | 100 mM Na-Acetate | 4 | 2 mg/ml PS80 | 3% Arg-HCl |
| 4 | 2 | 100 mM Na-Phosphate | 8 | — | 3% Arg-HCl |
| 5 | 10 | 10 mM Na-Acetate | 4 | 2 mg/ml PS80 | 3% Arg-HCl |
| 6 | 10 | 10 mM Na-Phosphate | 8 | — | 3% Arg-HCl |
| 7 | 10 | 100 mM Na-Acetate | 4 | — | — |
| 8 | 10 | 100 mM Na-Phosphate | 8 | 2 mg/ml PS80 | — |
| 9 | 2 | 10 mM Na-Acetate | 4 | 2 mg/ml PS80 | 300 mM NaCl/3% Arg-HCl |
| 10 | 2 | 10 mM Na-Phosphate | 8 | — | 300 mM NaCl/3% Arg-HCl |
| 11 | 2 | 100 mM Na-Acetate | 4 | 2 mg/ml PS80 | 300 mM NaCl |
| 12 | 2 | 100 mM Na-Phosphate | 8 | — | 300 mM NaCl |
| 13 | 10 | 10 mM Na-Acetate | 4 | 2 mg/ml PS80 | 300 mM NaCl |
| 14 | 10 | 10 mM Na-Phosphate | 8 | — | 300 mM NaCl |
| 15 | 10 | 100 mM Na-Acetate | 4 | — | 300 mM NaCl/3% Arg-HCl |
| 16 | 10 | 100 mM Na-Phosphate | 8 | 2 mg/ml PS80 | 300 mM NaCl/3% Arg-HCl |

A thermal stress test was performed with the samples prepared above. After the thermal stress test (storage at 37° C. for 2 weeks), the turbidity analysis by visual inspection, and DLS, SE-HPLC and IE-HPLC analyses were conducted to select the three main factors influencing aggregation and particle formation.

For the selection of the main factors, Minitab software was used in such a manner as to analyze the results from the pareto chart (alpha=0.15). The results are shown in FIGS. 2A and 2B, and FIGS. 3A and 3B.

Figure 2A:
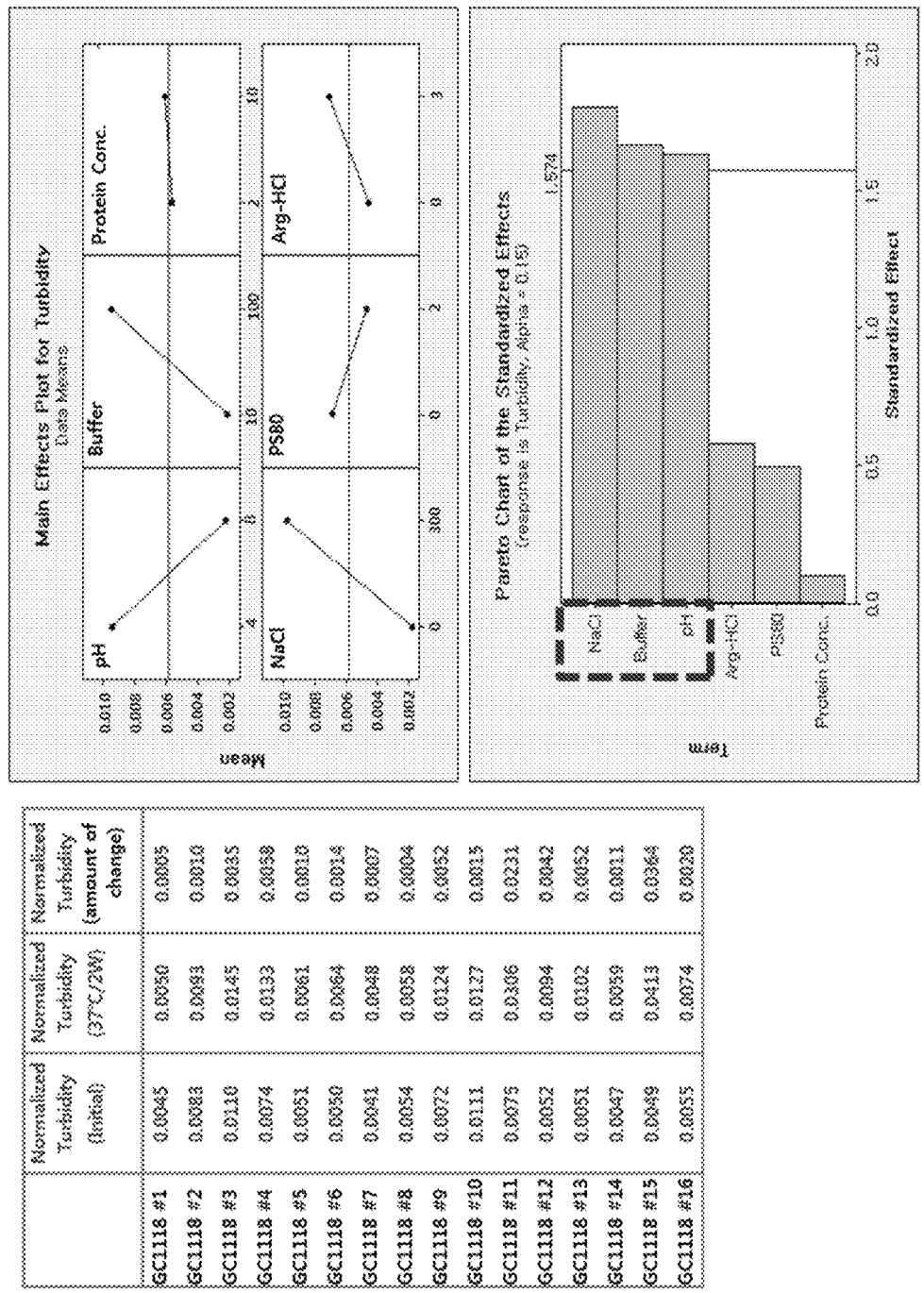
FIGS. 2A and 2B respectively show the results of turbidity and DLS analysis using the samples prepared for the selection of factors associated with aggregation and particle formation.
Figure 2B:
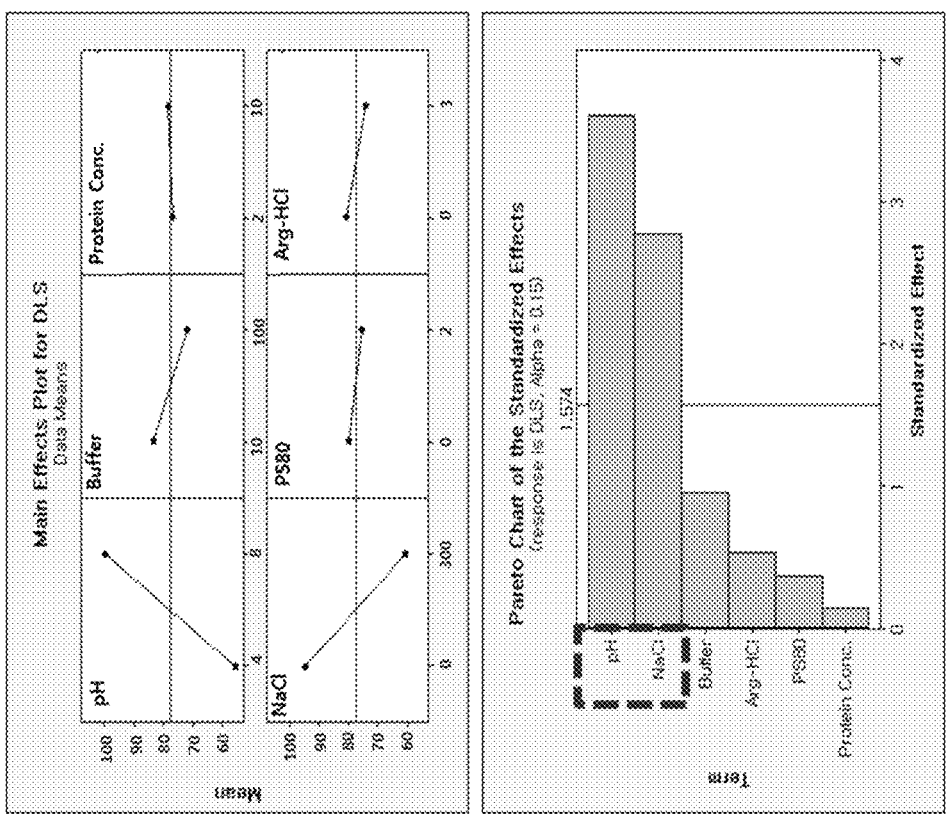

As shown in FIG. 2, the main factors influencing turbidity were NaCl, buffer concentration and pH (FIG. 2A). Also, DLS analysis results indicated that the main factors influencing the reduction of monomer intensity were pH and NaCl (FIG. 2B).

Figure 3A:
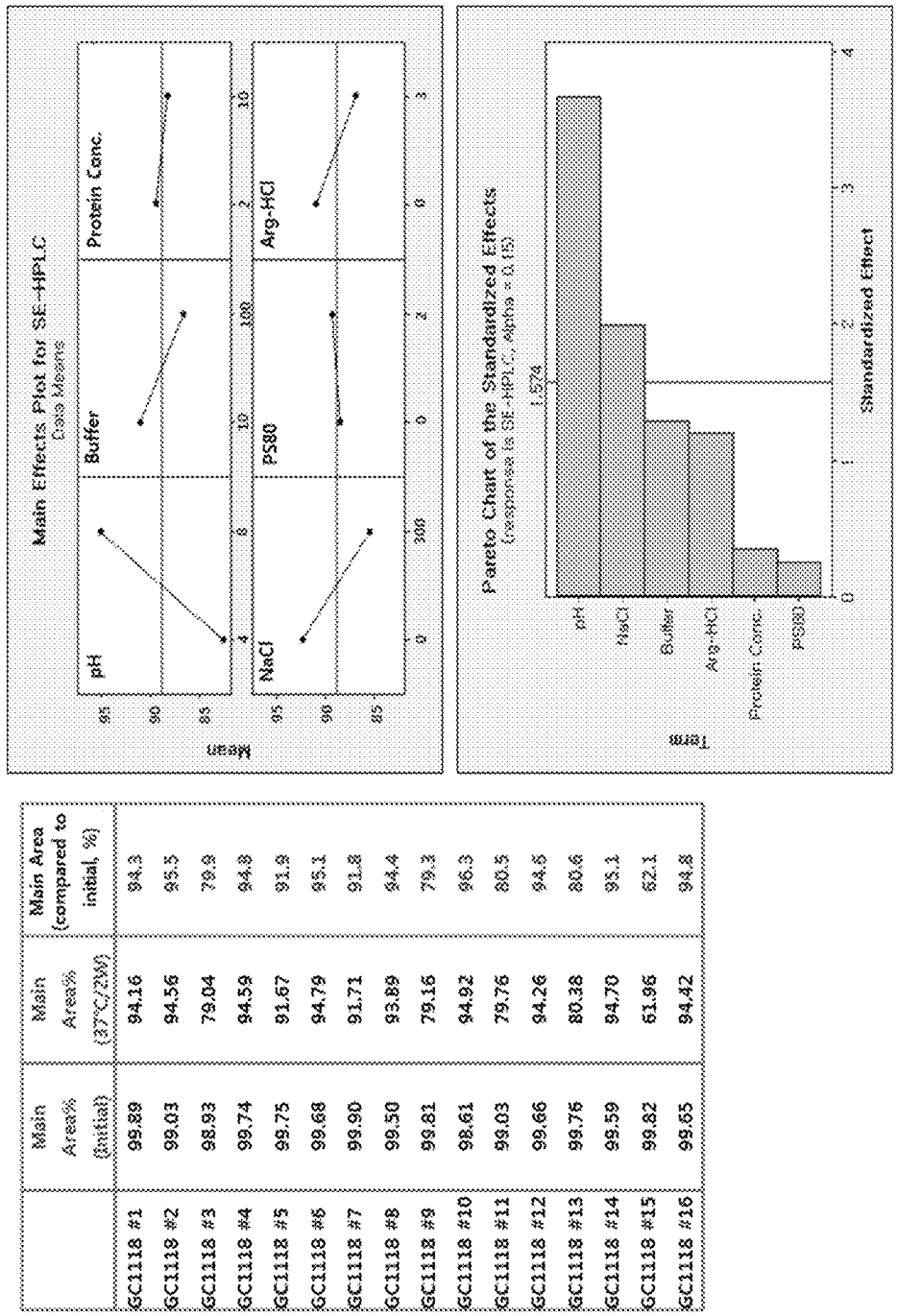
FIGS. 3A and 3B respectively show the results of SE-HPLC and IE-HPLC analysis using these samples.
Figure 3B:
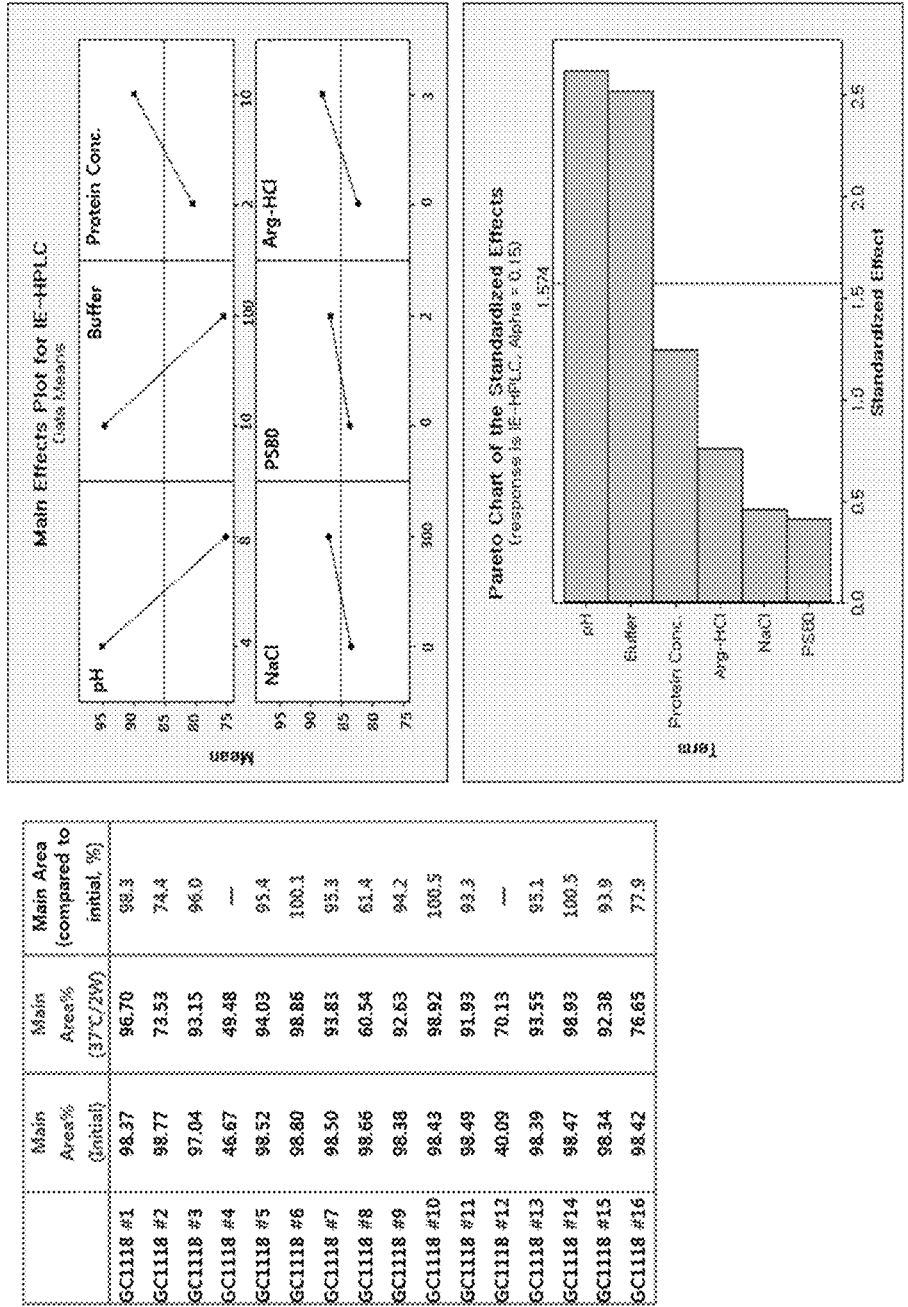

In addition, as shown in FIG. 3, the SE-HPLC analysis results indicated that the main factors influencing the main peak reduction were pH and NaCl (FIG. 3A). Also, IE- HPLC analysis results indicated that the main factors influencing the main peak reduction were pH and buffer concentration (FIG. 3B).

Based on the results, pH, NaCl and buffer concentration were selected as the main factors influencing aggregation and particle formation. In the following experiments, Response Surface Methodology (RSM) design was conducted using Minitab program.

Example 3: Selection of Conditions for Pharmaceutical Formulation by RSM Design In order to examine the main factors influencing aggregation and particle formation selected in Example 2 with regard to an optimized condition for a stable liquid formulation under a thermal stress, RSM design was conducted by Minitab program (CCI, level 5), and various samples were prepared in accordance with to the pH (4-8), and concentrations of NaCl (0-300 mM) and buffer (10-100 mM).

Specific ingredients of the samples prepared are described in Table 3 below.

TABLE 3

| No | Protein concentration (mg/ml) | Buffer | pH | Tonicifier |
|---|---|---|---|---|
| 1 | 10 mg/ml | 28 mM Na-Acetate | 4.8 | 61 mM NaCl |
| 2 | | 28 mM Na-Phosphate | 7.2 | 61 mM NaCl |
| 3 | | 82 mM Na-Acetate | 4.8 | 61 mM NaCl |
| 4 | | 82 mM Na-Phosphate | 7.2 | 61 mM NaCl |
| 5 | | 28 mM Na-Acetate | 4.8 | 239 mM NaCl |
| 6 | | 28 mM Na-Phosphate | 7.2 | 239 mM NaCl |
| 7 | | 82 mM Na-Acetate | 4.8 | 239 mM NaCl |
| 8 | | 82 mM Na-Phosphate | 7.2 | 239 mM NaCl |
| 9 | | 55 mM Na-Acetate | 4.0 | 150 mM NaCl |
| 10 | | 55 mM Na-Phosphate | 8.0 | 150 mM NaCl |
| 11 | | 10 mM Na-Acetate | 6.0 | 150 mM NaCl |
| 12 | | 100 mM Na-Acetate | 6.0 | 150 mM NaCl |
| 13 | | 55 mM Na-Acetate | 6.0 | — |
| 14 | | 55 mM Na-Acetate | 6.0 | 300 mM NaCl |
| 15 | | 55 mM Na-Acetate | 6.0 | 150 mM NaCl |
| 16 | | 55 mM Na-Acetate | 6.0 | 150 mM NaCl |
| 17 | | 55 mM Na-Acetate | 6.0 | 150 mM NaCl |
| 18 | | 55 mM Na-Acetate | 6.0 | 150 mM NaCl |
| 19 | | 55 mM Na-Acetate | 6.0 | 150 mM NaCl |
| 20 | | 55 mM Na-Acetate | 6.0 | 150 mM NaCl |

First, each sample was prepared by mixing the ingredients as indicated in Table 3. The prepared samples were subjected to thermal tests, under the storage condition of: (i) 37° C. for two weeks; or (ii) 60° C. for one day.

The results of visual inspection, protein concentration, SE-HPLC, IE-HPLC, IEF and SDS-PAGE analyses of each sample under the storage condition of 37° C. for two weeks are shown in FIGS. 9-14. Visual inspection analysis result revealed that only #9 was opaque while all others were colorless and transparent, and IEF results revealed that #9 showed band dragging phenomenon caused by particle formation.

The results of visual inspection, turbidity and DLS analysis, and binding assay 1 of each sample under the storage condition of 60° C. for one day are shown in FIGS. 15-18. Visual inspection analysis showed that turbidity was in the order of #9>#5>#7>#1 and #3 (all other samples were colorless and transparent), and the binding assay 1 result showed that #15 sample had $EC_{50}$% of 114 to 121% as compared to a control group.

Figure 19:
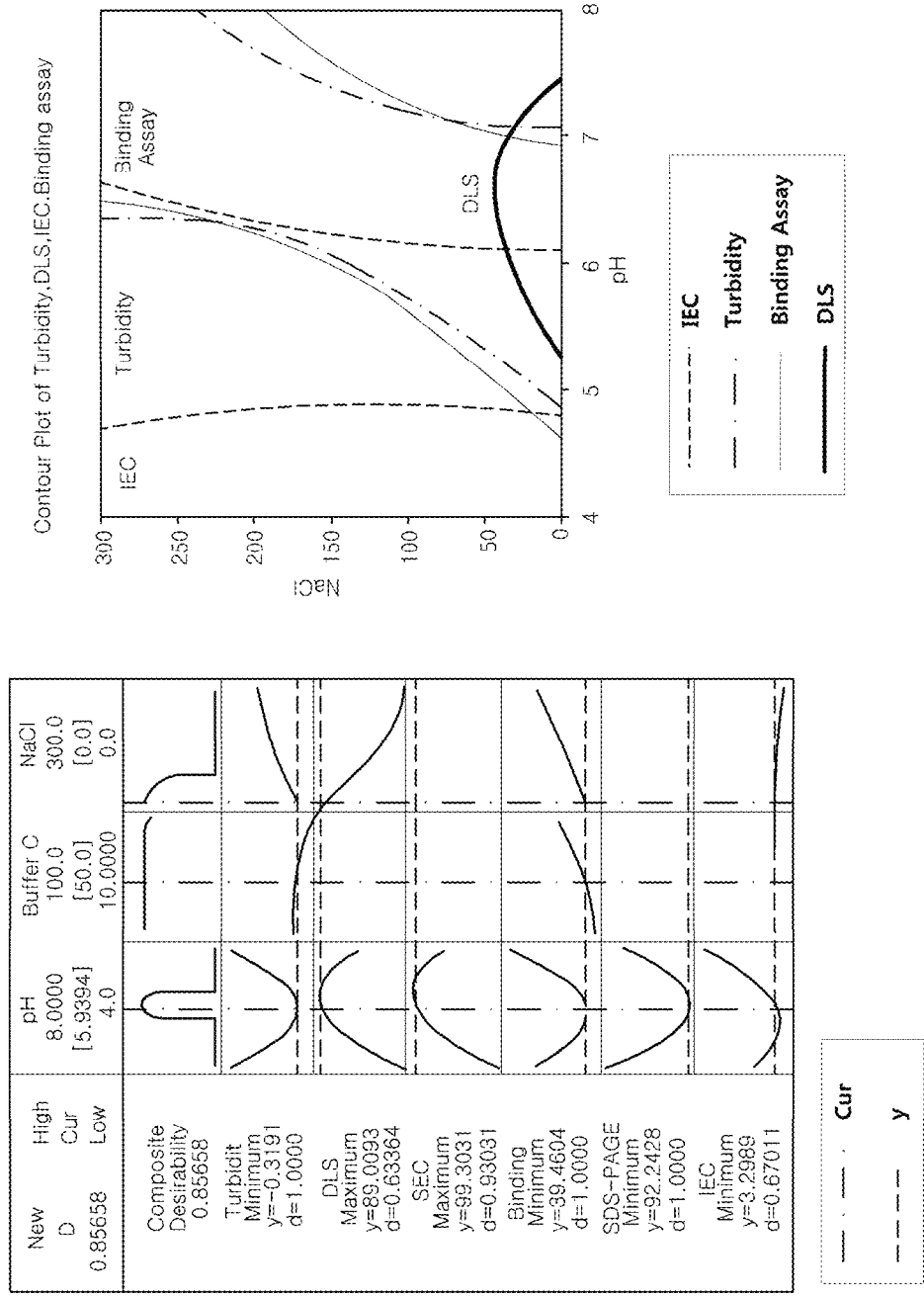
FIG. 19 shows the result of the optimized plot of the samples prepared by RSM design.

In addition, an optimized plot based on the above results is shown in FIG. 19 and Table 4.

TABLE 4

| | 37° C., 2 weeks | 60° C., 1 day |
|---|---|---|
| Turbidity | pH (p = 0.004), $R^2$ = 0.4749 | pH, NaCl (p = 0.001), $R^2$ = 0.8296 |
| DLS | pH (p = 0.001), $R^2$ = 0.5482 | pH, NaCl (p < 0.001), $R^2$ = 0.9286 |
| Protein concentration | No concentration change as compared to initial (±4% range) | — |
| SE-HPLC | pH (p < 0.001), $R^2$ = 0.6019 | — |
| IE-HPLC | pH, NaCl (P < 0.001), $R^2$ = 0.9486 | — |
| SDS-PAGE | pH (p < 0.001), $R^2$ = 0.6257 | — |
| IEF | No band pattern change as compared to initial (except #9, particle formation) | — |
| Binding Assay | pH, Buffer (p = 0.116), $R^2$ = 0.3715 | pH, NaCl (p < 0.001), $R^2$ = 0.8506 |
| Cell based Assay | — | — |

The conditions of a preferred pharmaceutical preparation suggested by the statistical analysis based on the results of Table 4 are shown in Table 5 below.

TABLE 5

| | Protein concentration | Buffer solution | pH | Tonicifier |
|---|---|---|---|---|
| Optimized plot base | 10 mg/ml | 10-94 mM Na-Acetate | 5.94 | no NaCl |
| Contour base | 10 mg/ml | 10-100 mM Na-Acetate | 5.3-6.1 | 0 mM NaCl |

More particularly, the condition satisfying a desired potency while minimizing aggregation, particle formation, and potential variation under the thermal stress condition was found to be protein (anti-EGFR antibody) concentration of 10 mg/ml, 10 to 100 mM sodium acetate, pH of 5.3 to 6.1, and 0 mM NaCl (based on contour). Also, the optimum safety condition among the above conditions was pH of 5.94, 50 mM sodium acetate, and no NaCl (i.e., 0 mM NaCl) (based on optimized plot).

Example 4: Screening of the Type of Tonicifier

To select the type of a tonicifier to be used in the pharmaceutical formulation according to the present invention, each sample was prepared by mixing the ingredients as shown in Table 6. The prepared samples were stored at 60° C. for one day, and then the results of visual inspection, turbidity, and DLS analysis are shown in FIGS. 4A, 4B, and 4C, respectively.

TABLE 6

| No | Protein concentration | Buffer | pH | Tonicifier | Note |
|---|---|---|---|---|---|
| 1 | 10 mg/ml | 50 mM Na-Acetate | 5.8 | — | Control |
| 2 | 10 mg/ml | 50 mM Na-Acetate | 5.8 | 110 mM NaCl | Current temporary formulation |
| 3 | 10 mg/ml | 50 mM Na-Acetate | 5.8 | 3% Glycine | Tonicifier change (Isotonic level) |
| 4 | | 50 mM Na-Acetate | 5.8 | 3% Arg-HCl | |
| 5 | | 50 mM Na-Acetate | 5.8 | 5% Mannitol | |
| 6 | | 50 mM Na-Acetate | 5.8 | 5% Sorbitol | |
| 7 | | 50 mM Na-Acetate | 5.8 | 5% Trehalose | |

Figure 4B:
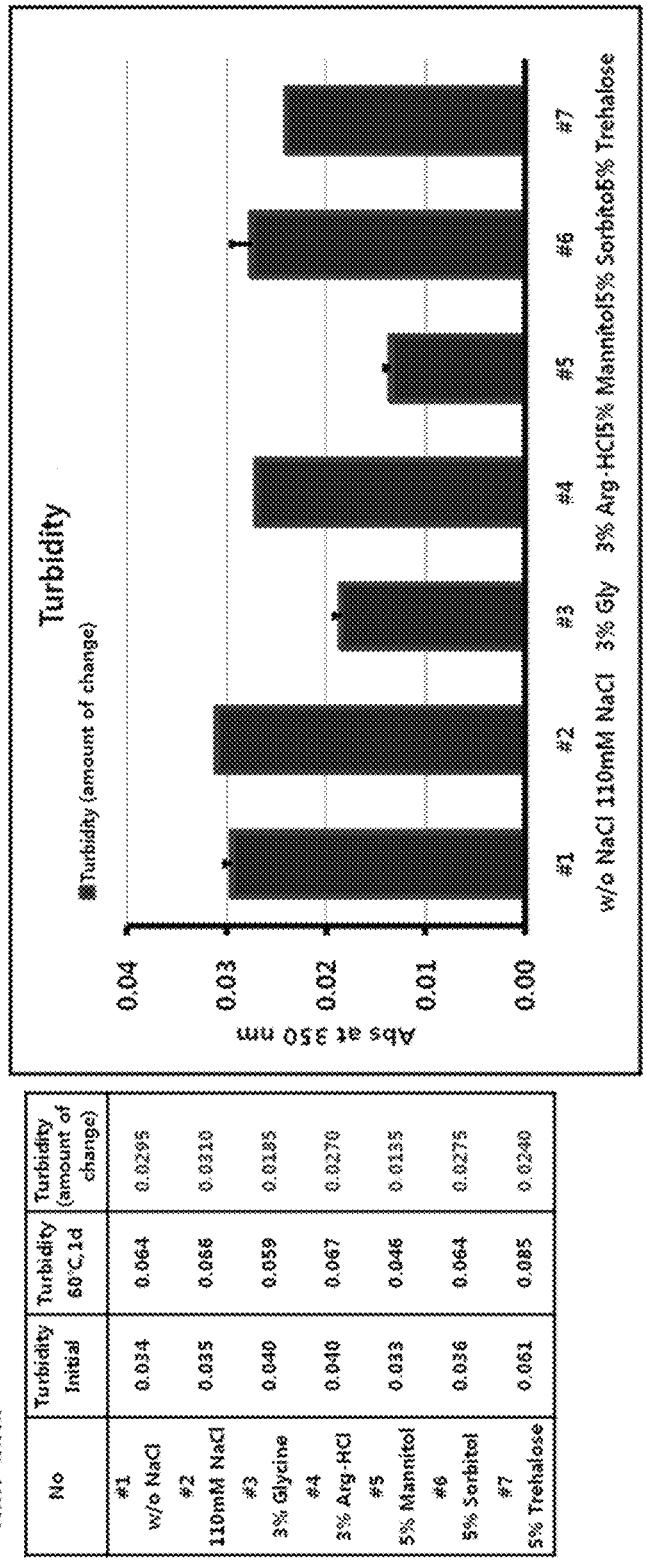
Figure 4C:
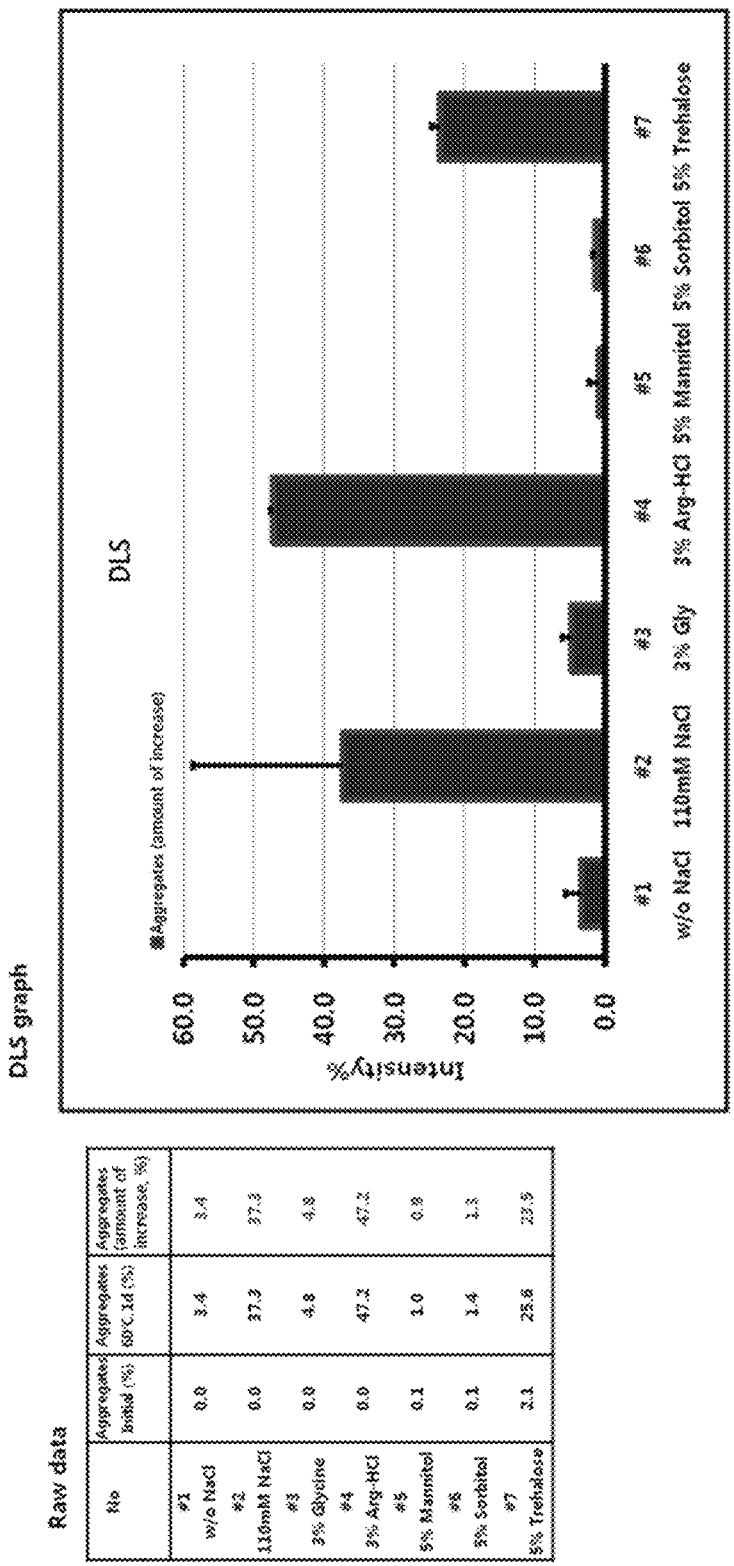

As shown in FIG. 4, visual inspection analysis result showed that all samples were colorless and transparent (FIG. 4A), and turbidity and DLS analysis results showed that the formulations containing 3% glycine or 5% mannitol significantly inhibited the increase in turbidity (FIGS. 4B and 4C).

Example 5: Determination of Concentration of Polysorbate 80

To determine the concentration of polysorbate 80 to be used in a pharmaceutical formulation according to the present invention, each sample was prepared by mixing the ingredients as shown in Table 7. Then the prepared samples were subjected to mechanical tests, and the results of visual inspection, turbidity, and DLS analysis are shown in FIGS. 5A, 5B, and 5C, respectively.

TABLE 7

| No | Protein concentration (mg/ml) | Buffer | pH | Surfactant | Tonicifier |
|----|------|------|------|------|------|
| 1 | 12.60 | 50 mM Na-Acetate | 5.8 | — | 110 mM NaCl |
| 2 | | | | 0.05 mg/ml Polysorbate 80 | |
| 3 | | | | 0.1 mg/ml Polysorbate 80 | |
| 4 | | | | 0.2 mg/ml Polysorbate 80 | |
| 5 | | | | 0.5 mg/ml Polysorbate 80 | |
| 6 | | | | 1.0 mg/ml Polysorbate 80 | |
| 7 | | | | 2.0 mg/ml Polysorbate 80 | |

Figure 5A:
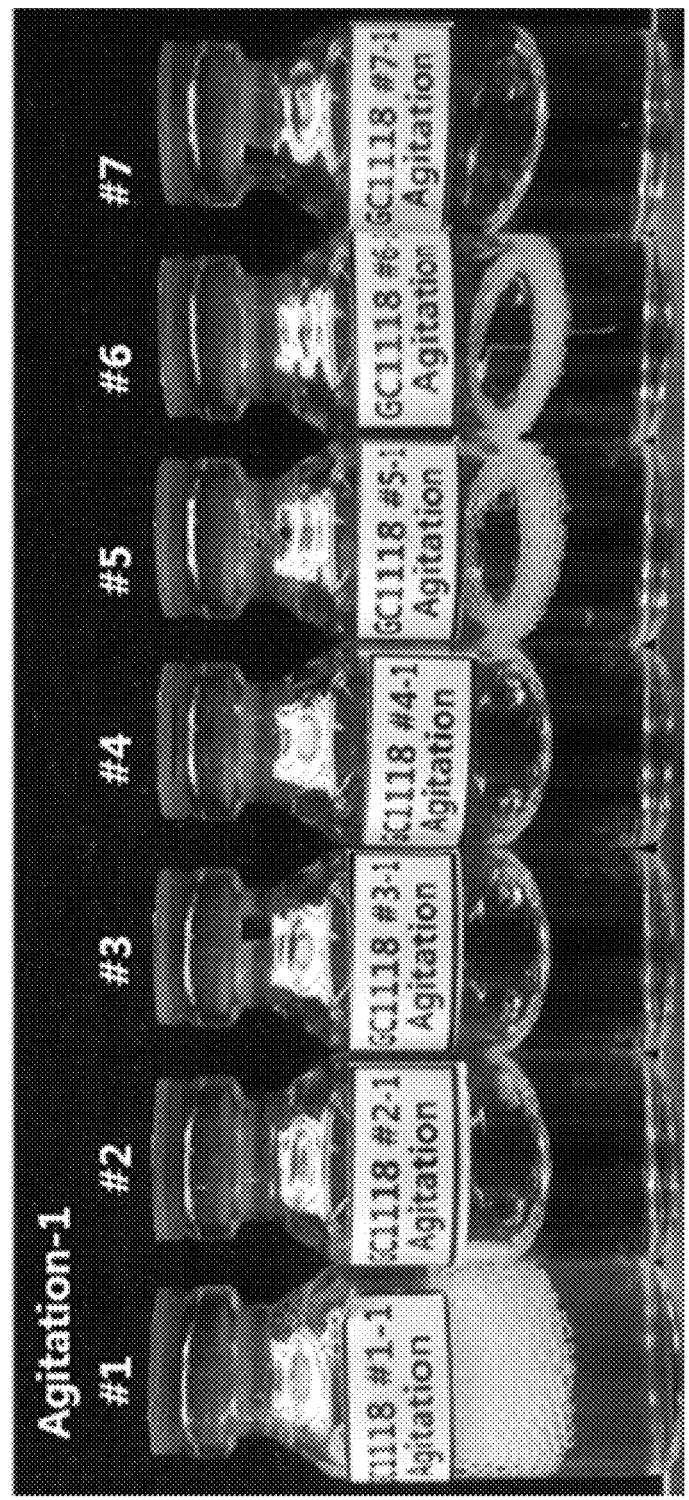
Figure 5B:
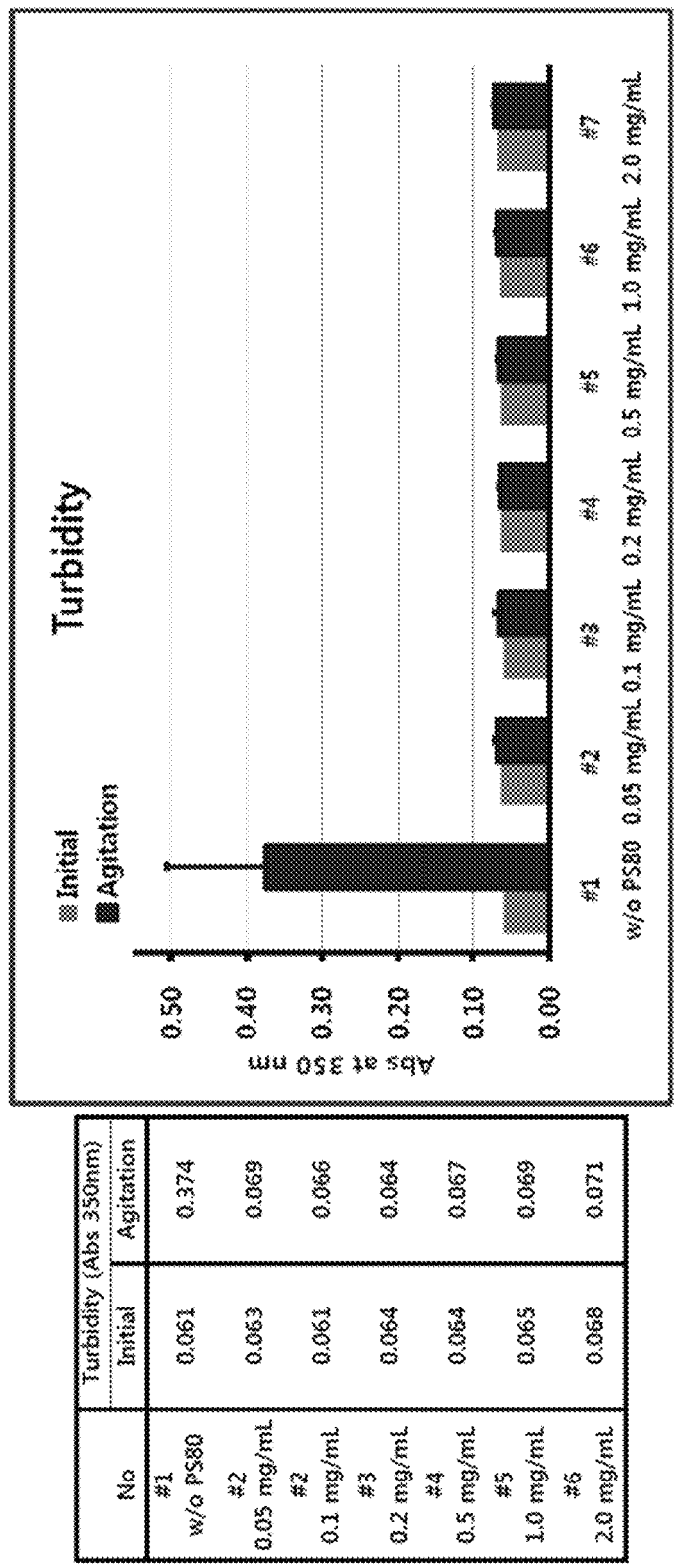

As shown in FIG. 5, only sample #1 was opaque and all other samples were colorless and transparent (FIG. 5A). In addition, there was no significant turbidity change except in sample #1, and turbidity inhibition effect was observed throughout the concentration range of 0.05 to 2.0 mg/ml (FIG. 5B). Meanwhile, DLS analysis result also revealed that the aggregation inhibition effect was observed throughout the concentration range of 0.05 to 2.0 mg/ml (FIG. 5C).

Among them, 0.2 mg/ml of polysorbate 80 resulted in the lowest aggregation and was chosen as the optimum concentration.

Preparation Examples 1 to 3 and Comparative Preparation Examples 1 and 2: Preparation of Pharmaceutical Formulations Pharmaceutical liquid formulations were prepared in a conventional manner using the ingredients as shown in Table 8.

TABLE 8

| | Protein concentration | Buffer | pH | Surfactant | Tonicifier |
|---|---|---|---|---|---|
| Comparative Preparation Example 1 (Temporary formulation #1) | 10.0 mg/ml | 50 mM Na-Acetate | 5.8 | — | 110 mM NaCl |
| Comparative Preparation Example 2 (Temporary formulation #2) | | | | 0.2 mg/ml polysorbate 80 (PS80) | 110 mM NaCl |
| Preparation Example 1 (#3, no NaCl and PS80) | 10.0 mg/ml | 50 mM Na-Acetate | 5.7 (±0.4) | 0.2 mg/ml PS80 | no NaCl |
| Preparation Example 2 (#4, Glycine and PS80) | | | | 0.2 mg/ml PS80 | 3% Glycine |
| Preparation Example 3 (#5, Mannitol and PS80) | | | | 0.2 mg/ml PS80 | 5% Mannitol |

Test Example: Stability Analysis of Pharmaceutical Formulations

After storage of the pharmaceutical formulations prepared in accordance with Preparation Examples 1 to 3 and Comparative Preparation Examples 1 and 2 under the stress conditions described below, visual inspection, turbidity, DLS, protein content, SE-HPLC, IE-HPLC, SDS-PAGE, IEF and potencies 1 and 2 analyses were conducted.

Stress Conditions (1) storage at 60° C. for 2 weeks (1 day, 3 days, 1 week and 2 weeks)

(2) storage at 5° C., 25° C. or 37° C. for 2 weeks to 12 months (initial, 2 weeks, 4 weeks, 6 weeks, 8 weeks, and 3 to 12 months)

Results

Under the condition of storage at 60° C. for two weeks, visual inspection analysis results revealed that the pharmaceutical formulations of Comparative Preparation Examples 1 and 2 became opaque, whereas the pharmaceutical formulation of Preparation Example 3 remained colorless and transparent after 2-week storage. Turbidity and DLS analysis indicated that the pharmaceutical formulation of Preparation Example 3, which contained mannitol and polysorbate 80, showed the smallest increase in turbidity (FIGS. 6A and 6B).

Under the condition of storage at 5° C., 25° C. or 37° C. for 2 weeks to 12 months, visual inspection analysis result revealed that all pharmaceutical formulations were colorless and transparent under any of the storage conditions. Turbidity change analysis of the formulations stored at different temperatures indicated that the samples stored at 5° C. or 25° C. showed no change in turbidity regardless of the type of the formulation. However, among the samples stored at 37° C., formulation #4 of Preparation Example 2 showed a 2.3-fold increase in turbidity after 8-week storage as compared to the initial point (FIG. 7).

On the other hand, the UV protein quantitative analysis revealed that all formulations under any of the temperature conditions were in the range of 95 to 105% as compared to the initial point, showing no significant changes.

Figure 8A:
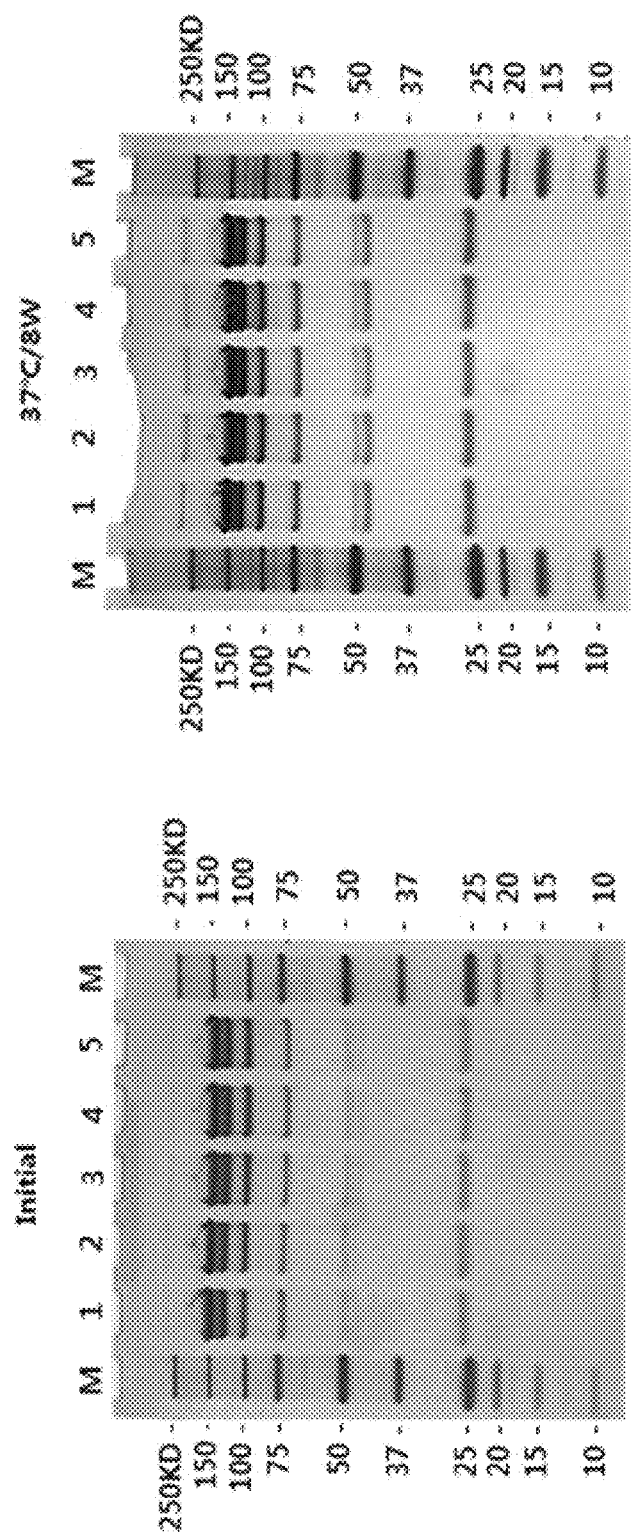
Figure 9:
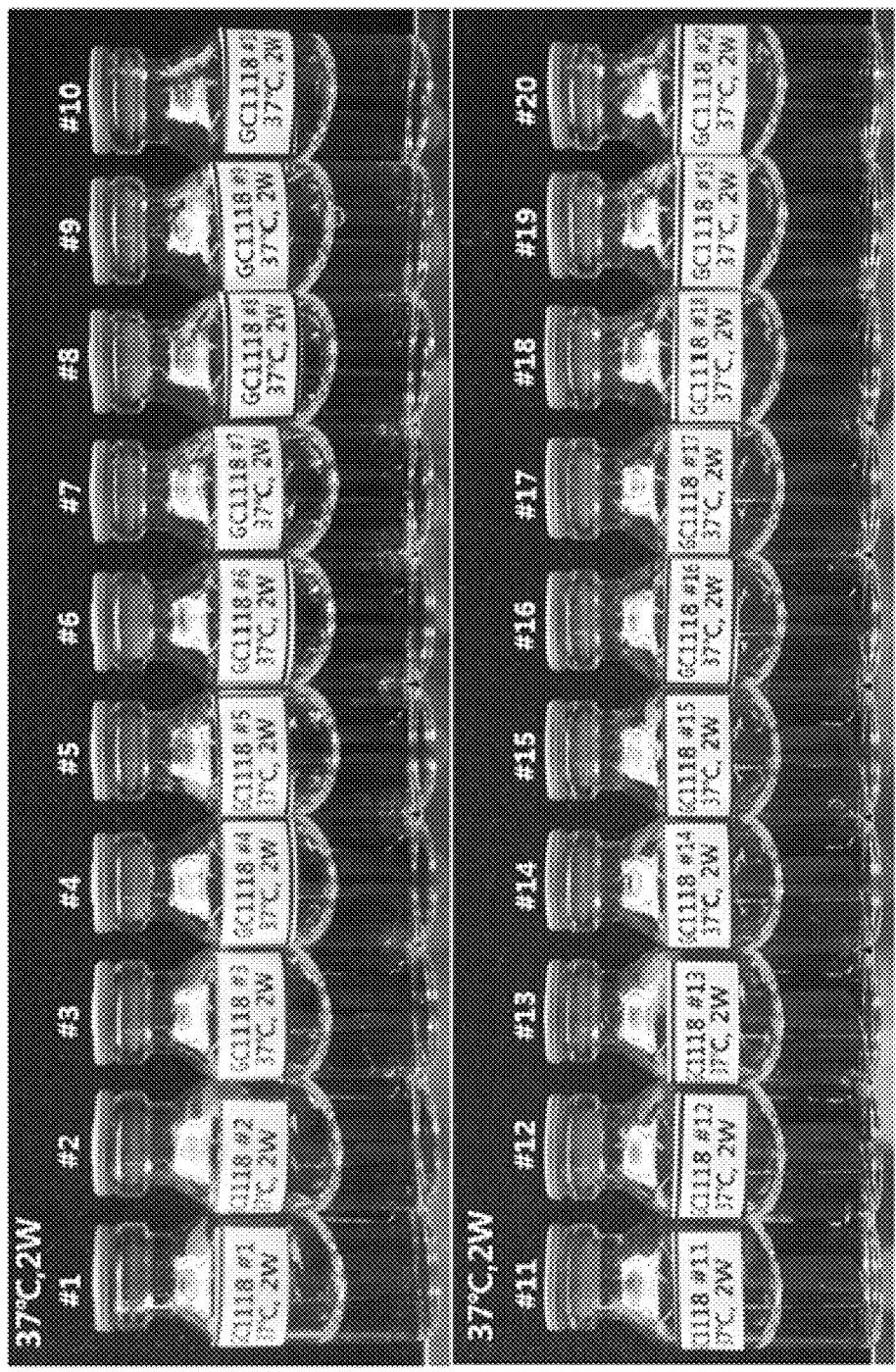
Figure 11:
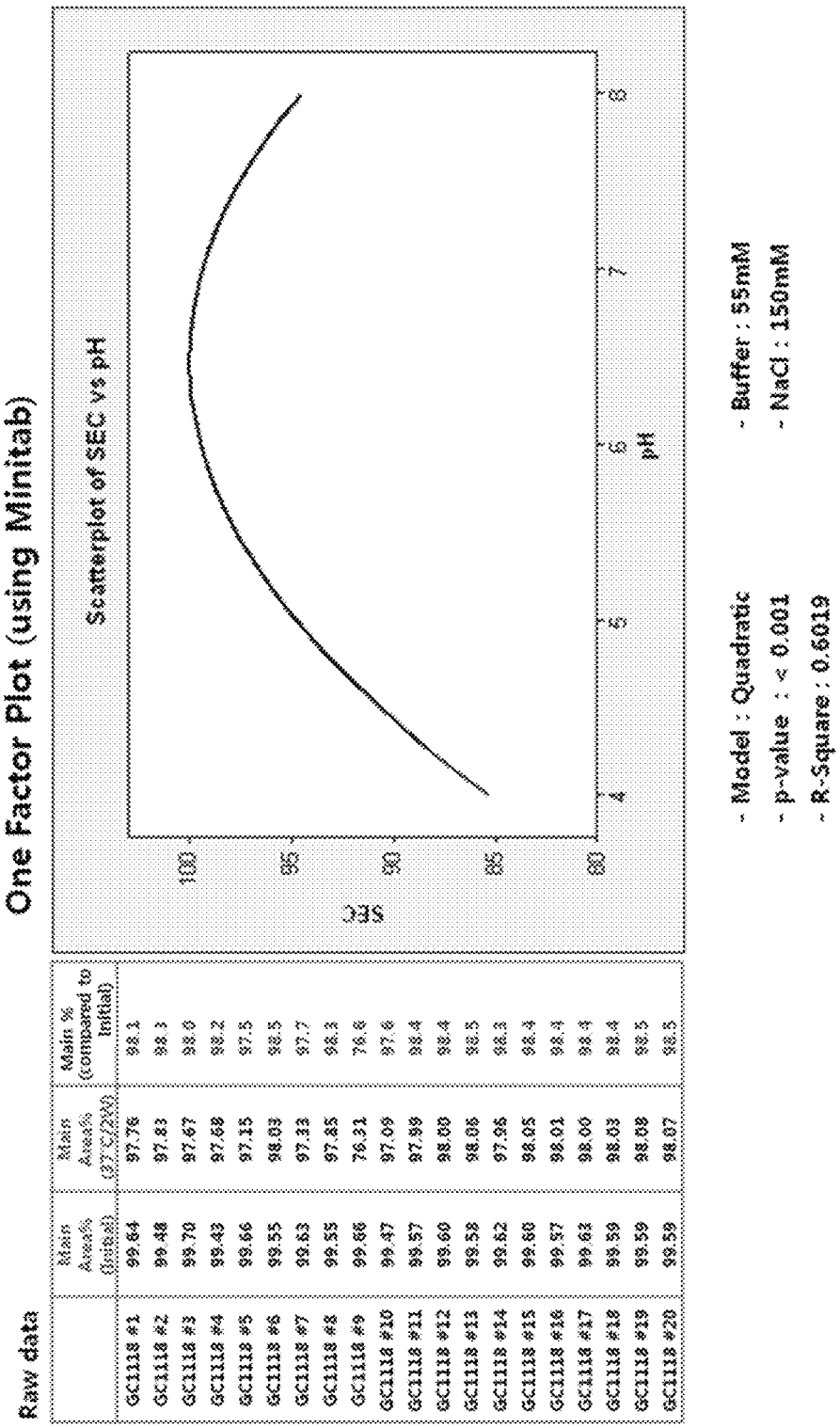
Figure 12:
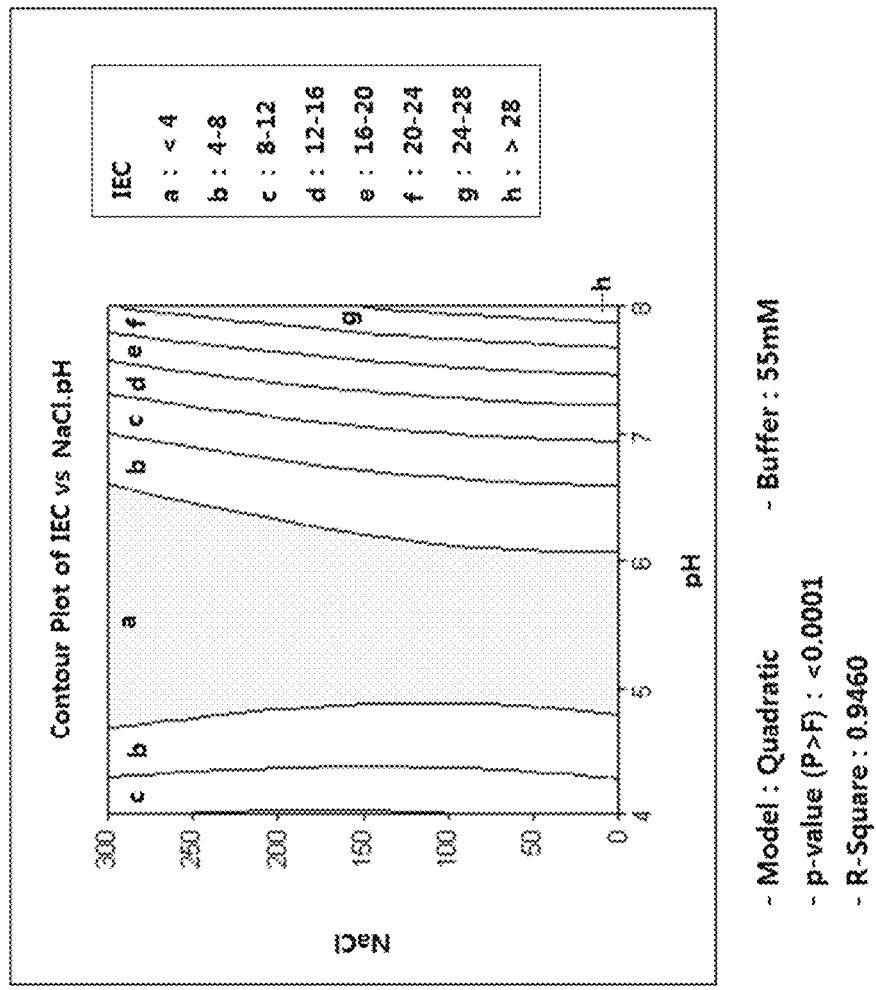
Figure 13C:
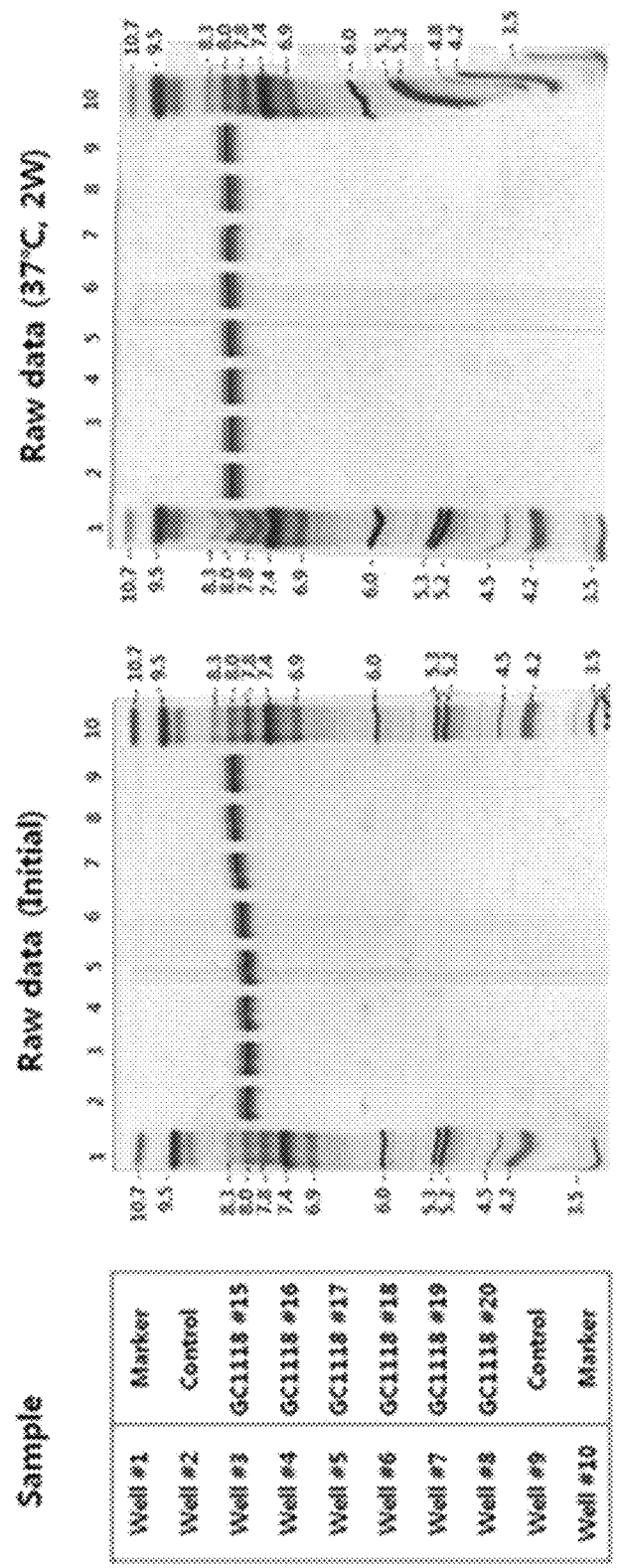
Figure 14:
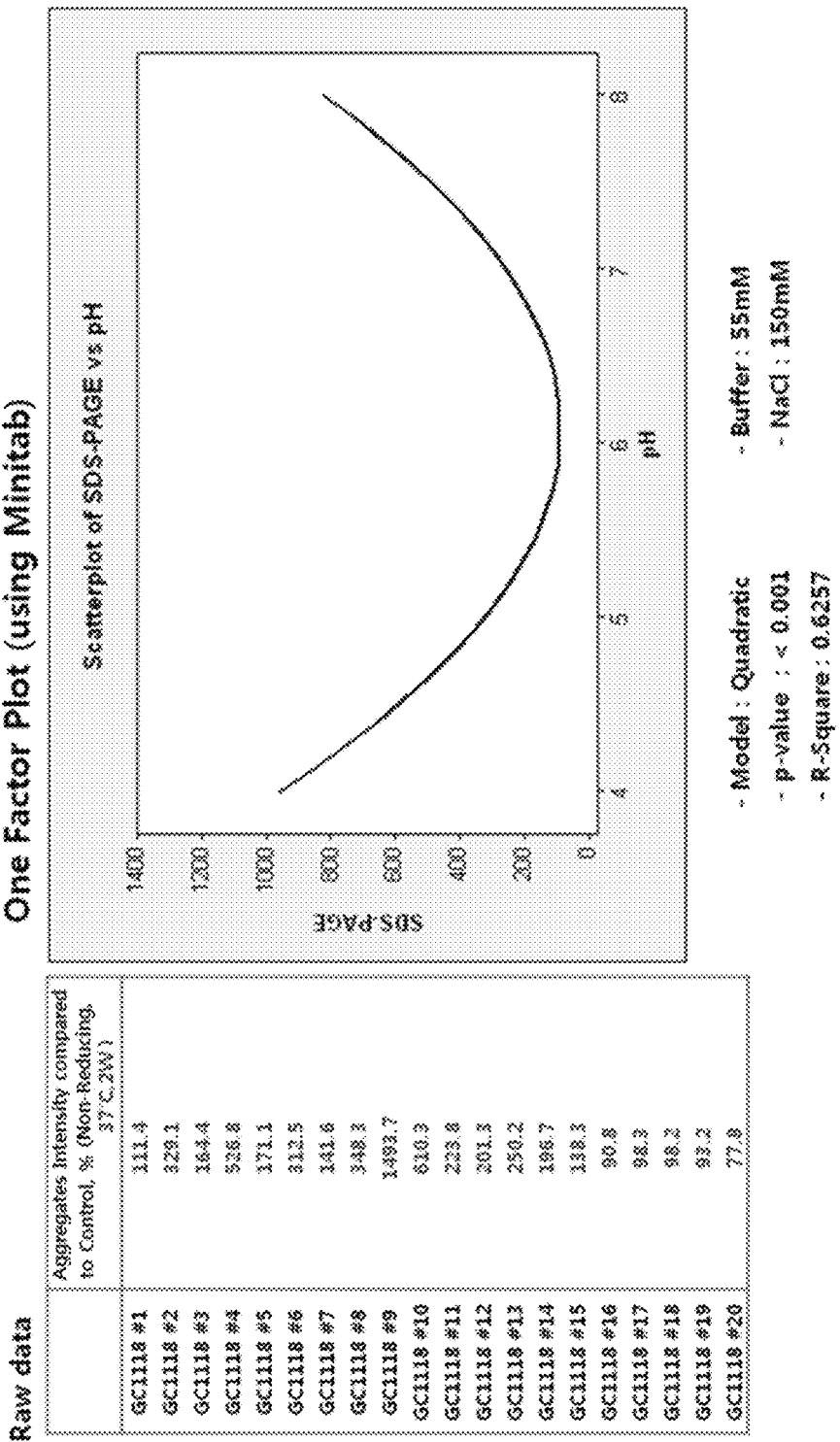
Figure 15:
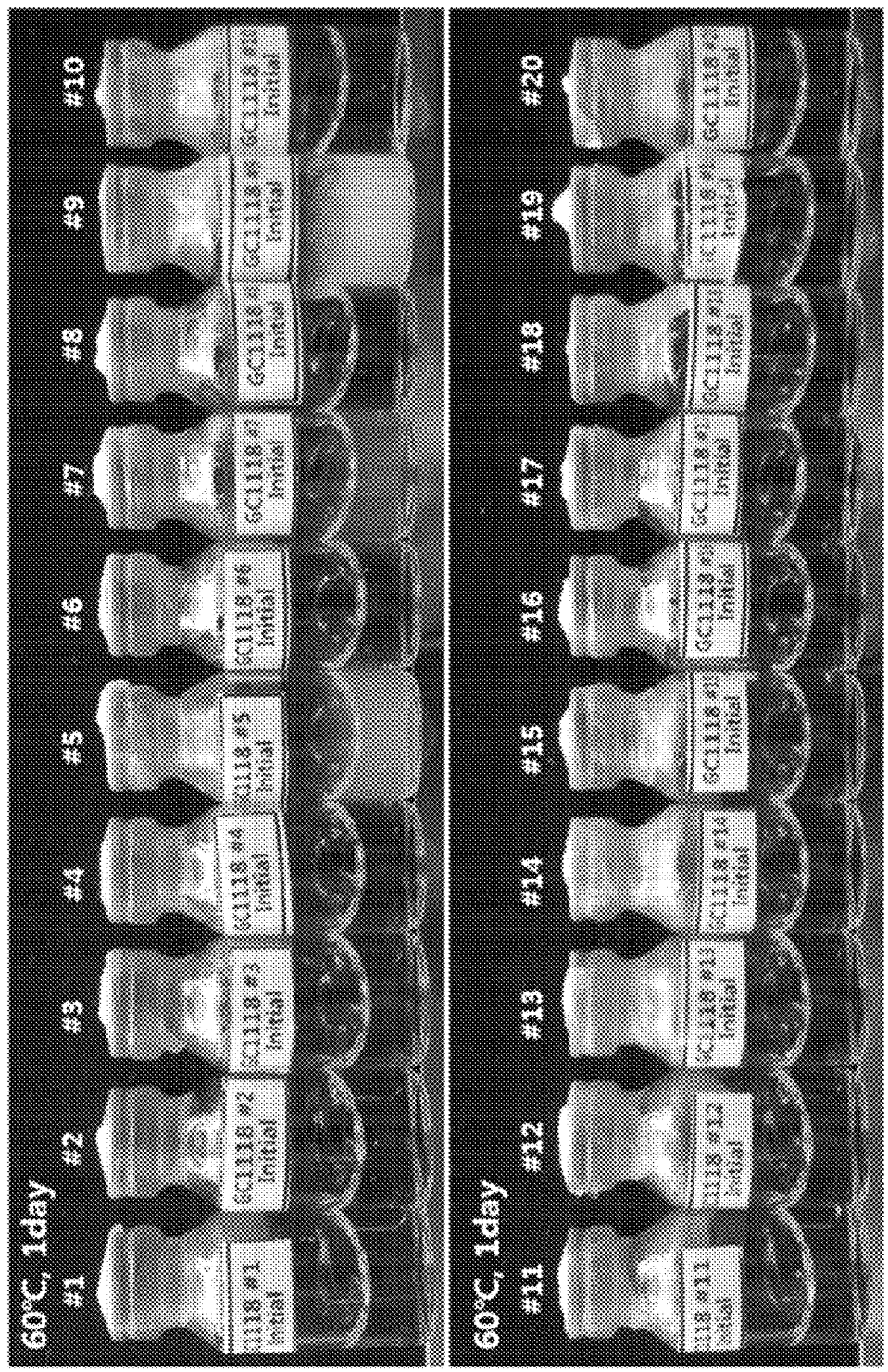
FIGS. 15, 16, 17 and 18 respectively show the results of visual inspection, turbidity, DLS and potency 1 (binding assay) analysis of each sample prepared by RSM design under the storage condition of 60° C. for 1 day.
Figure 16:
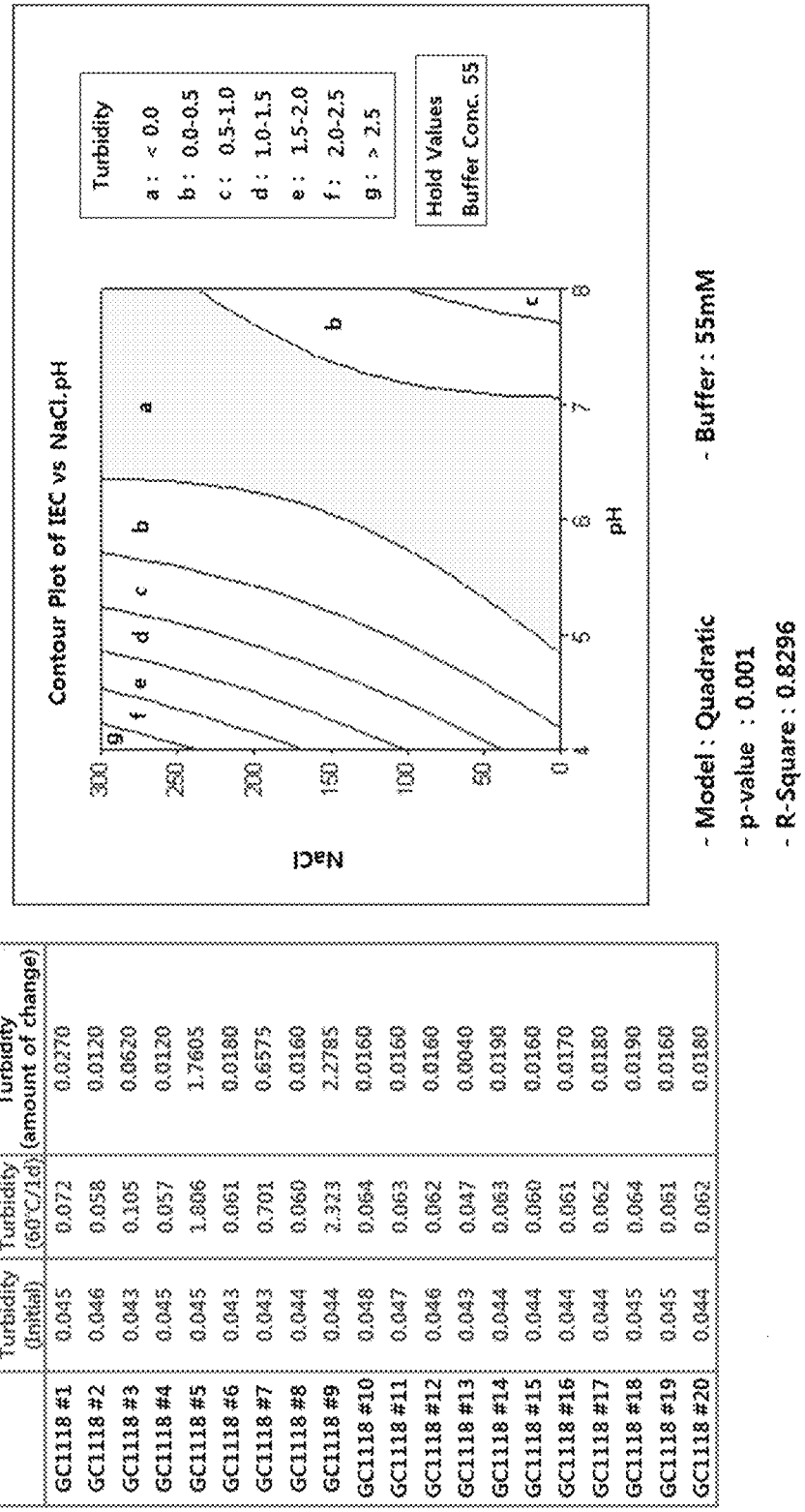
Figure 17:
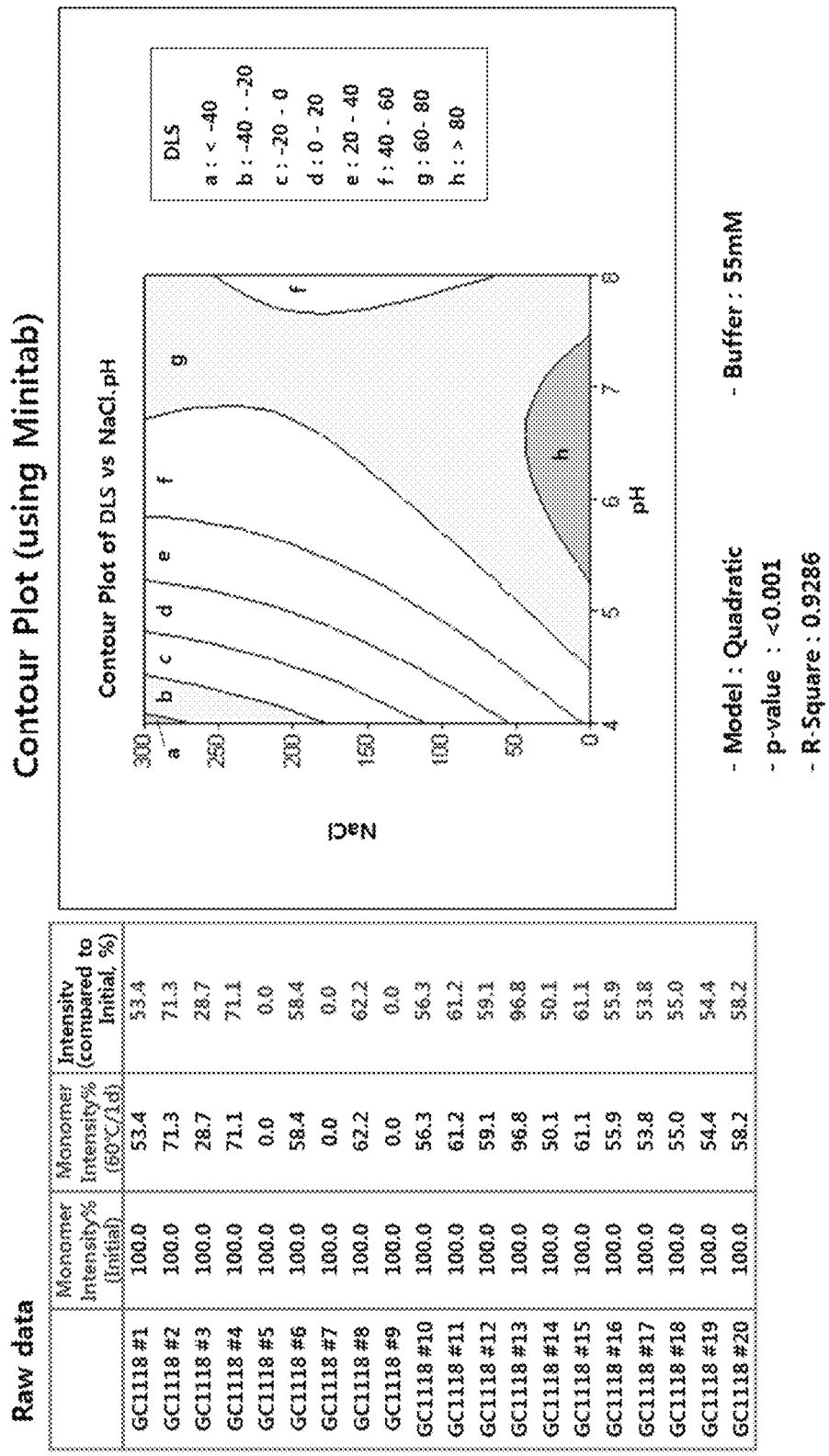
Figure 18:
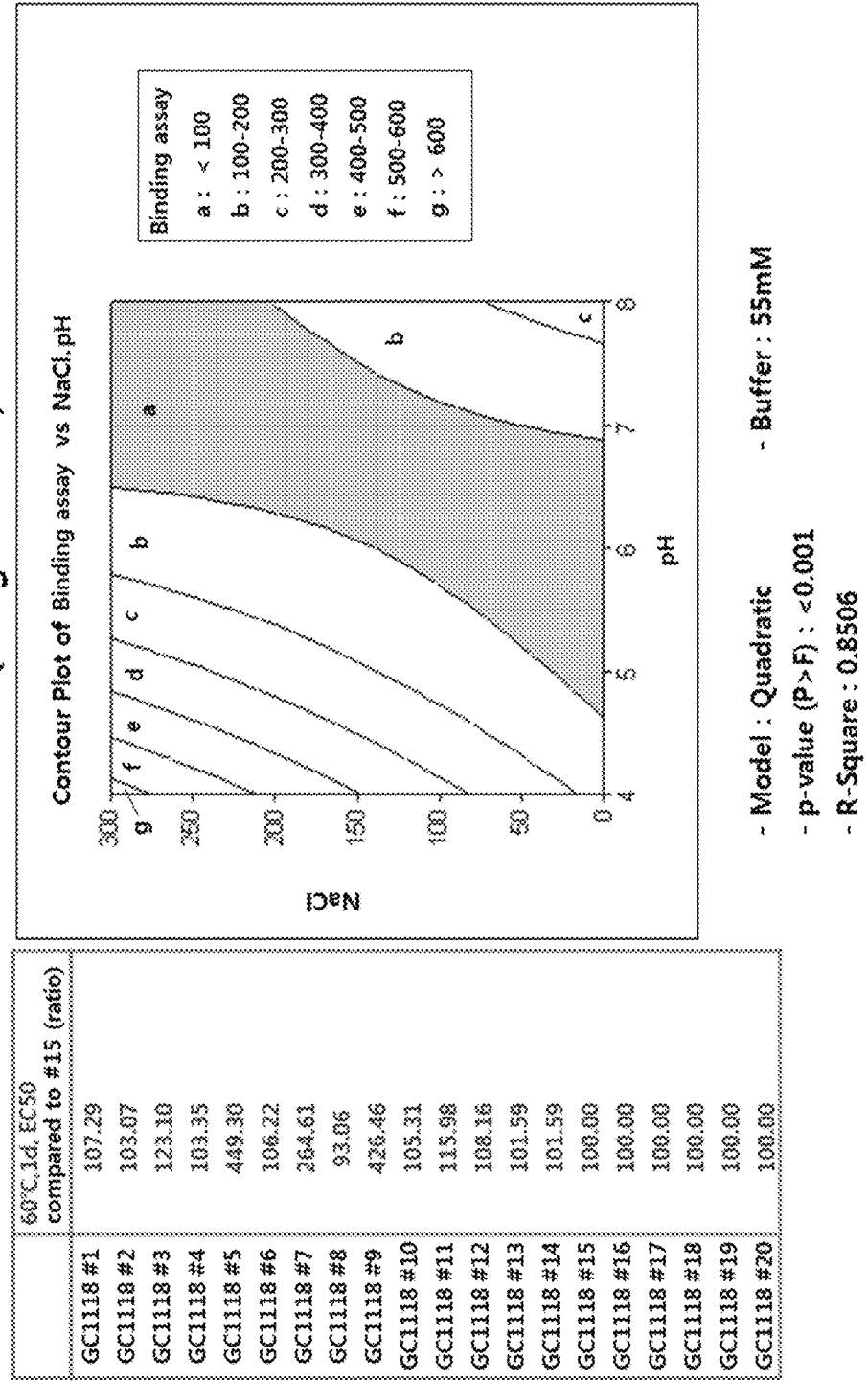

The SDS-PAGE analysis result indicated that there was no difference in the band patterns according to storage temperatures between the Preparation Examples and Comparative Preparation Examples. However, as can be seen from FIGS. 8A and 8B, the results at initial point and after 8-week storage at 37° C. under non-reducing and reducing conditions indicated differences in the band patterns between the samples at the initial point and after the high temperature storage. Under the non-reducing condition, all of the formulations #1 to #5 of the Preparation Examples and Comparative Preparation Examples after storage at 37° C. showed increase in the band intensity at 250 kD, and 37 to 50 kD as compared to the initial point. Also, under the reducing condition, the formulations #1 to #5 of the Preparation Examples and Comparative Preparation Examples after storage at 37° C. showed increase in the band intensity at 75 kD, and new band formations at 25 to 50 kD, as compared to the initial point.

Meanwhile, IEF results indicated that there was no difference in IEF band patterns between the formulations or according to different temperatures under any of the storage conditions, and the bands were located between the pI of 7.8 to 8.3.

SE-HPLC analysis results indicated that all of the formulations #1 to #5 of the Preparation Examples and Comparative Preparation Examples showed no significant purity change after storage at 5° C. or 25° C. However, after storage at 37° C. for 8 weeks, formulations #1, #2, #3, #4 and #5 showed the values of 95.66%, 95.15%, 96.46%, 96.42% and 96.56%, respectively, which implies purity decreases of 3.14 to 4.55% as compared to the initial point. As such, it was found that the formulations of Preparation Examples of the present invention showed significantly higher stability as compared to the Comparative Preparation Examples. Particularly, the formulations of Comparative Preparation Examples showed large amount of purity decrease, which was caused by the increase of pre-peak portion (presumed to be aggregations) preceding the main peak.

The potency 2 analysis (cell-based assay) results revealed that all the formulations, regardless of the storage temperature, showed $EC_{50}$ of 70 to 130% as compared to the control group, indicating that there was no significant change.

The above results indicates that a tonicifier for inhibiting the aggregation and particle formation under the heat stress condition for use in a pharmaceutical formulation comprising an anti-EGFR antibody may be NaCl, glycine, mannitol, or the like, preferably, mannitol or no NaCl; and the preferred concentration of polysorbate 80 for inhibiting the aggregation and particle formation under the mechanical stress condition is 0.2 mg/ml.

Also, the result of stability analysis of the pharmaceutical formulations after storage at the high temperature of 60° C. indicated that a formulation comprising 10 mg/ml an anti-EGFR antibody can be stabilized under the mechanical/thermal stress by containing 50 mM sodium acetate, pH of 5.7±0.4, 0.2 mg/ml polysorbate 80 and 5% mannitol.

In addition, the result of stability analysis of the pharmaceutical formulations after storage at 5° C., 25° C. and 37° C. for 8 weeks indicated that it is preferable for the formulation comprising 10 mg/ml anti-EGFR antibody to further contain 50 mM sodium acetate, pH 5.7±0.4, 0.2 mg/ml polysorbate 80, without containing NaCl in terms of physical/chemical stability.

The invention claimed is:

1. A pharmaceutical formulation comprising an anti-epidermal growth factor receptor (EGFR) antibody, sodium acetate anhydrous, and polysorbate 80, wherein the anti-EGFR antibody is comprised in a concentration of 2 to 10 mg/ml,
   wherein the anti-EGFR antibody is GC1118A;
   wherein the sodium acetate anhydrous is comprised in a concentration of 50 to 100 mM;
   wherein no sodium chloride (NaCl) is included in the pharmaceutical formulation; and
   wherein the pharmaceutical formulation shows a greater stability compared to a same pharmaceutical composition except for comprising sodium chloride under storage conditions of 60° C. for two weeks; and
   wherein the pH of the pharmaceutical formulation ranges from pH 5.3 to 6.1.

2. The pharmaceutical formulation of claim 1, which further comprises a tonicifier selected from mannitol, glycine or a combination thereof.

3. The pharmaceutical formulation of claim 1, wherein the polysorbate 80 is comprised in a concentration of 0.05 to 2.0 mg/ml.

4. The pharmaceutical formulation of claim 2, wherein the tonicifier is mannitol and is comprised in a concentration of 1 to 20% (w/v).

5. The pharmaceutical formulation of claim 2, wherein the tonicifier is glycine and is comprised in a concentration of 1 to 10% (w/v).

6. The pharmaceutical formulation of claim 2, wherein the tonicifier is a mixture of mannitol and glycine which are mixed in a weight ratio of 5:1 to 1:5, and is comprised in a concentration of 1 to 10% (w/v).

* * * * *